US011707227B2

(12) United States Patent
Luxon et al.

(10) Patent No.: US 11,707,227 B2
(45) Date of Patent: Jul. 25, 2023

(54) DEVICES AND METHODS FOR MONITORING PHYSIOLOGIC PARAMETERS

(71) Applicant: Respirix, Inc., San Francisco, CA (US)

(72) Inventors: Evan S. Luxon, Omaha, NE (US); Daniel R. Burnett, San Francisco, CA (US); Alexander Vergara, San Francisco, CA (US); Mark Ziegler, Palo Alto, CA (US); Nikhil Viswanathan, San Francisco, CA (US); Michael Hemati, San Francisco, CA (US)

(73) Assignee: Respirix, Inc., San Francisco, CA (US)

( * ) Notice: Subject to any disclaimer, the term of this patent is extended or adjusted under 35 U.S.C. 154(b) by 0 days.

(21) Appl. No.: 15/863,722

(22) Filed: Jan. 5, 2018

(65) Prior Publication Data
US 2018/0140252 A1    May 24, 2018

Related U.S. Application Data

(63) Continuation of application No. PCT/US2016/061993, filed on Nov. 15, 2016.
(Continued)

(51) Int. Cl.
*A61B 5/00* (2006.01)
*A61B 5/087* (2006.01)
(Continued)

(52) U.S. Cl.
CPC ............ *A61B 5/682* (2013.01); *A61B 5/0205* (2013.01); *A61B 5/0245* (2013.01);
(Continued)

(58) Field of Classification Search
None
See application file for complete search history.

(56) References Cited

U.S. PATENT DOCUMENTS

| | | | |
|---|---|---|---|
| 5,704,345 | A | 1/1998 | Berthon-Jones |
| 5,803,066 | A | 9/1998 | Rapoport et al. |

(Continued)

FOREIGN PATENT DOCUMENTS

| | | |
|---|---|---|
| JP | H2-195941 | 7/1995 |
| JP | 2015-033568 | 2/2015 |

(Continued)

OTHER PUBLICATIONS

Young et al. "Noninvasive Monitoring Cardiac Output Using Partial CO2 Rebreathing" (2010).
(Continued)

*Primary Examiner* — Michael R Bloch
(74) *Attorney, Agent, or Firm* — Levine Bagade Han LLP

(57) ABSTRACT

Devices and methods for monitoring physiologic parameters are described where an airway device, in one embodiment, may comprise a mouthpiece section and an opening section defining one or more airway lumens therethrough with a first sensor in fluid communication with the one or more airway lumens and a second sensor positioned upon a hand-piece for contact against a portion of the user. The first sensor may be configured to detect an airway pressure when a user inhales or exhales through the one or more airway lumens, and the second sensor may be configured to detect a physiological signal from the user. Additionally, a controller may be in communication with the first and second sensors where the controller is programmed to correlate pressure oscillations in the airway pressure with heartbeats.

46 Claims, 32 Drawing Sheets

Related U.S. Application Data

(60) Provisional application No. 62/402,244, filed on Sep. 30, 2016, provisional application No. 62/331,263, filed on May 3, 2016, provisional application No. 62/302,684, filed on Mar. 2, 2016, provisional application No. 62/264,734, filed on Dec. 8, 2015, provisional application No. 62/255,915, filed on Nov. 16, 2015.

(51) Int. Cl.
| | |
|---|---|
| A61B 5/03 | (2006.01) |
| A61B 5/08 | (2006.01) |
| A61B 5/352 | (2021.01) |
| A61B 5/0205 | (2006.01) |
| A61B 5/024 | (2006.01) |
| A61B 5/0245 | (2006.01) |
| A61B 5/097 | (2006.01) |
| A61M 16/06 | (2006.01) |
| A61M 16/00 | (2006.01) |
| G09B 19/00 | (2006.01) |
| A61B 5/318 | (2021.01) |
| A61B 5/349 | (2021.01) |
| A61B 5/145 | (2006.01) |
| A61B 5/1455 | (2006.01) |

(52) U.S. Cl.
CPC ............ *A61B 5/02416* (2013.01); *A61B 5/03* (2013.01); *A61B 5/0803* (2013.01); *A61B 5/087* (2013.01); *A61B 5/097* (2013.01); *A61B 5/352* (2021.01); *A61B 5/4884* (2013.01); *A61B 5/6826* (2013.01); *A61B 5/14507* (2013.01); *A61B 5/14551* (2013.01); *A61B 5/318* (2021.01); *A61B 5/349* (2021.01); *A61B 2562/0247* (2013.01); *A61M 16/00* (2013.01); *A61M 16/06* (2013.01); *A61M 2205/3569* (2013.01); *A61M 2205/3592* (2013.01); *A61M 2230/04* (2013.01); *A61M 2230/40* (2013.01); *G09B 19/003* (2013.01)

(56) References Cited

U.S. PATENT DOCUMENTS

| | | | |
|---|---|---|---|
| 5,931,160 A * | 8/1999 | Gilmore | A61M 16/0051 128/204.21 |
| 6,029,665 A | 2/2000 | Berthon-jones | |
| 6,159,147 A * | 12/2000 | Lichter | A61B 5/02055 600/300 |
| 6,186,956 B1 | 2/2001 | McNamee | |
| 6,238,349 B1 | 5/2001 | Hickey | |
| 6,253,764 B1 | 7/2001 | Calluaud | |
| 6,273,088 B1 * | 8/2001 | Hillsman | A61M 16/0051 128/204.23 |
| 6,428,483 B1 | 8/2002 | Carlebach | |
| 6,654,631 B1 | 11/2003 | Sahai | |
| 6,675,797 B1 | 1/2004 | Berthon-jones | |
| 6,733,464 B2 | 5/2004 | Olbrich et al. | |
| 6,832,113 B2 * | 12/2004 | Belalcazar | A61N 1/37252 607/17 |
| 7,077,810 B2 | 7/2006 | Lange et al. | |
| 7,282,032 B2 | 10/2007 | Miller | |
| 7,320,320 B2 | 1/2008 | Berthon-jones | |
| 7,730,886 B2 | 6/2010 | Berthon-jones | |
| 7,740,591 B1 | 6/2010 | Starr et al. | |
| 7,752,002 B2 | 7/2010 | Zhang et al. | |
| 7,787,946 B2 | 8/2010 | Stahmann et al. | |
| 8,069,852 B2 | 12/2011 | Burton et al. | |
| 8,343,057 B2 | 1/2013 | Starr et al. | |
| 8,343,064 B2 | 1/2013 | Bardy | |
| 8,360,060 B2 | 1/2013 | Berthon-jones | |
| 8,381,722 B2 | 2/2013 | Berthon-jones | |
| 8,424,527 B1 | 4/2013 | Kayyali et al. | |
| 8,545,416 B1 * | 10/2013 | Kayyali | A61B 5/085 128/204.23 |
| 8,644,915 B2 | 2/2014 | Chou | |
| 8,794,236 B2 | 8/2014 | Phuah et al. | |
| 8,831,715 B2 | 9/2014 | Boege et al. | |
| 8,894,231 B2 | 11/2014 | Kwok | |
| 8,938,299 B2 | 1/2015 | Christopherson et al. | |
| 9,026,190 B2 | 5/2015 | Shenasa et al. | |
| 9,220,856 B2 | 12/2015 | Martin et al. | |
| 9,549,678 B2 | 1/2017 | Silber | |
| 2005/0256417 A1 * | 11/2005 | Fischell | A61B 5/0031 600/510 |
| 2006/0047210 A1 | 3/2006 | Moroki et al. | |
| 2006/0074333 A1 * | 4/2006 | Huiku | A61B 5/0205 600/529 |
| 2006/0084877 A1 * | 4/2006 | Ujhazy | A61M 16/0051 600/483 |
| 2007/0191697 A1 * | 8/2007 | Lynn | A61B 5/0205 600/323 |
| 2008/0066753 A1 * | 3/2008 | Martin | A61M 16/026 128/204.23 |
| 2008/0305464 A1 | 12/2008 | Lynn | |
| 2009/0007916 A1 * | 1/2009 | Ralfs | A61B 5/0205 128/204.23 |
| 2010/0036266 A1 | 2/2010 | Myklebust et al. | |
| 2010/0331716 A1 * | 12/2010 | Watson | A61B 5/02416 600/538 |
| 2011/0015496 A1 | 1/2011 | Sherman et al. | |
| 2011/0054277 A1 * | 3/2011 | Pinter | A61B 5/0205 600/310 |
| 2011/0295083 A1 * | 12/2011 | Doelling | A61B 5/103 600/301 |
| 2013/0025597 A1 * | 1/2013 | Doyle | A61M 16/00 128/204.23 |
| 2014/0000606 A1 | 1/2014 | Doyle et al. | |
| 2014/0155764 A1 * | 6/2014 | Silber | A61B 5/0205 600/484 |
| 2014/0202455 A1 | 7/2014 | Garde et al. | |
| 2014/0228657 A1 | 8/2014 | Palley et al. | |
| 2014/0276120 A1 | 9/2014 | Starr et al. | |
| 2014/0364758 A1 | 12/2014 | Schindhelm et al. | |
| 2015/0018632 A1 | 1/2015 | Khair | |
| 2015/0018660 A1 | 1/2015 | Thomson et al. | |
| 2015/0034082 A1 * | 2/2015 | Kimm | A61M 16/0051 128/202.16 |
| 2015/0182713 A1 | 7/2015 | Phuah et al. | |
| 2015/0258370 A1 * | 9/2015 | Arkush | A61B 5/486 482/8 |
| 2016/0067433 A1 | 3/2016 | Martin et al. | |
| 2017/0209074 A1 * | 7/2017 | Siu | A61B 5/08 |

FOREIGN PATENT DOCUMENTS

| | | |
|---|---|---|
| JP | 2015-508672 | 3/2015 |
| JP | 2015-526114 | 9/2015 |
| WO | WO 2005/079897 | 9/2005 |
| WO | WO 2015/134895 | 9/2015 |
| WO | WO 2016/073945 | 5/2016 |

OTHER PUBLICATIONS

Gesche, Heiko, et al. "Continuous blood pressure measurement by using the pulse transit time: comparison to a cuff-based method." (2011).

Gesche et al. "Continuous blood pressure measurement by using the pulse transit time: comparison to a cuff-based method." (2011).

Young et al. "Noninvasive Monitoring Cardiac Output Using Partial CO2 Rebreathing." Critical Care Clinic (2010): 383-392.

\* cited by examiner

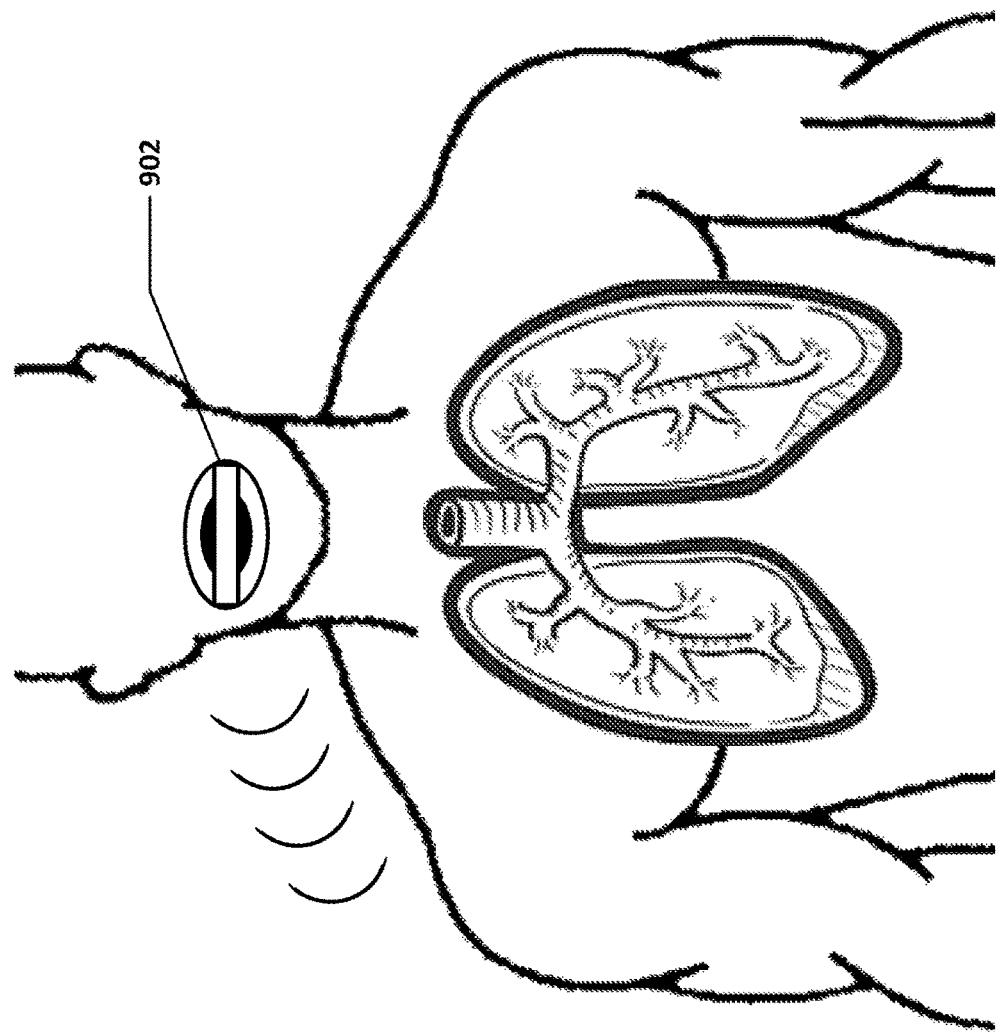
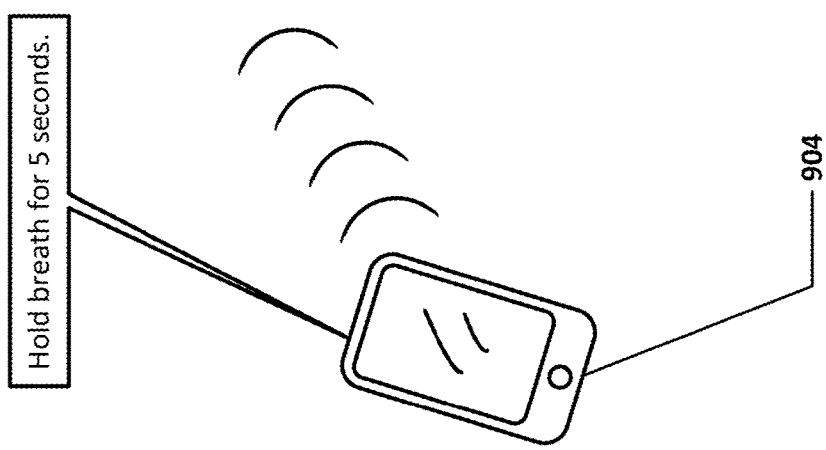
FIG. 9

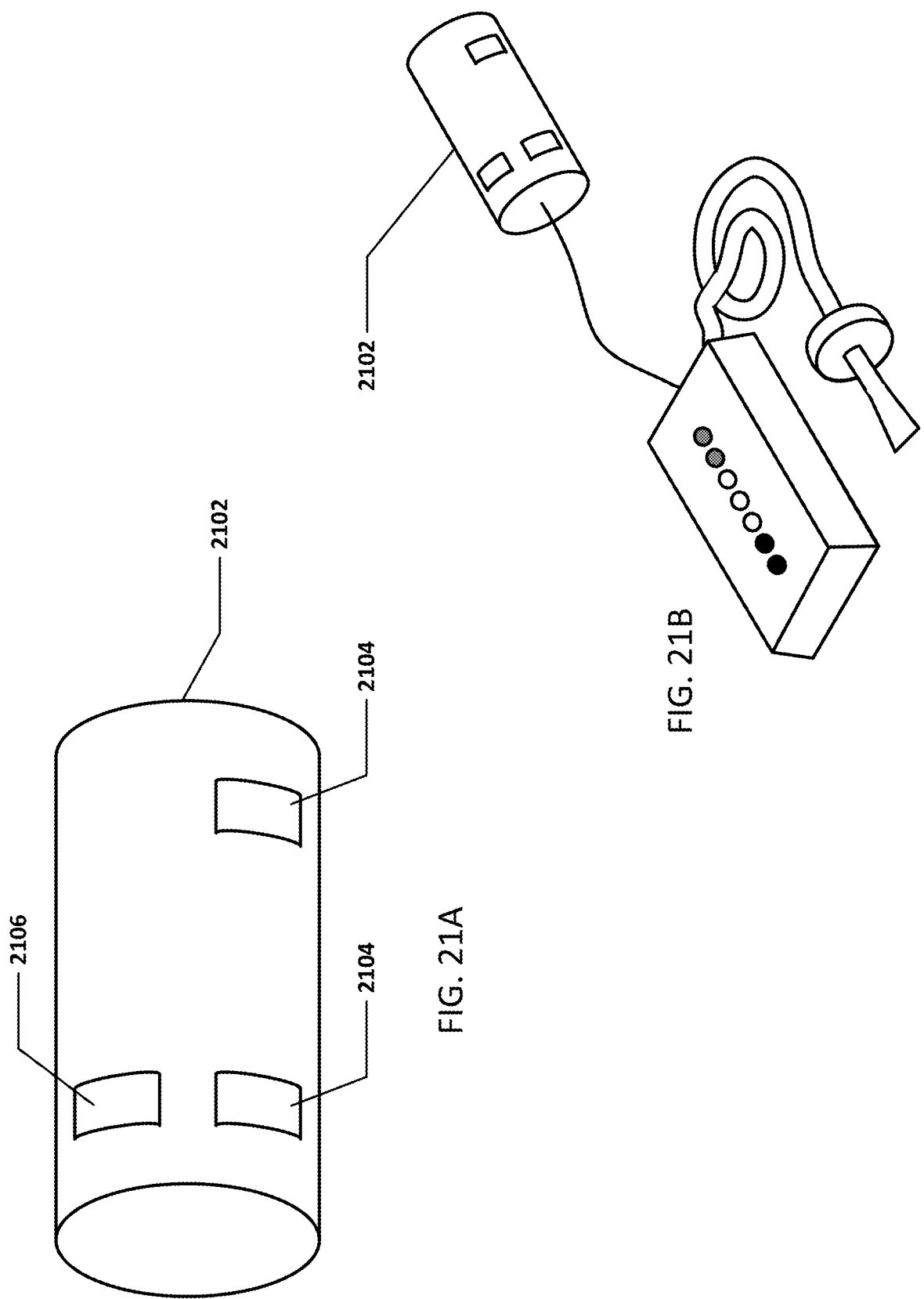

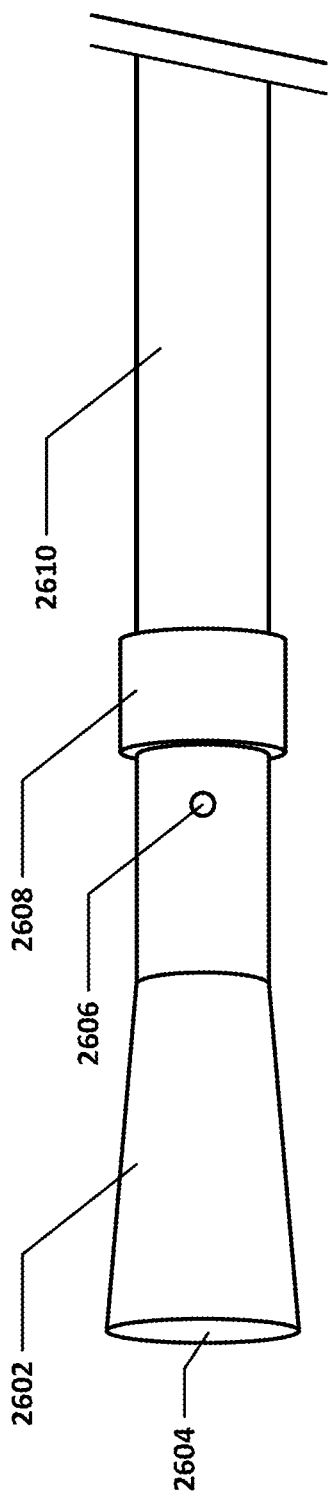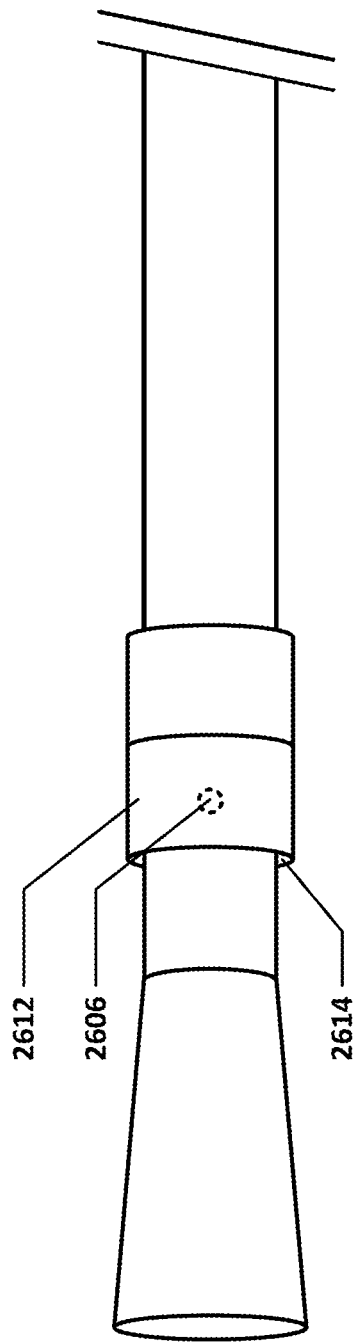

Please Check all that apply:
- ☐ Difficulty breathing
- ☐ Cough
- ☐ Congenstion
- ☐ Flu
- ☐ Common cold
- ☐ Asthma
- ☐ Infection
- ☐ Allergies
- ☐ Other Submit

FIG. 35

Did your heart failure prevent you from living as you wanted during the past month by:

- Causing swelling in your ankles, legs, etc.?
- Making your walking around the house or yard difficult?
- Making your relating to or doing things with your friends or family difficult?
- Making you sit or lie down to rest during the day?
- Making you tired, fatigued or low on energy?
- Making your working to earn a living difficult?
- Making your walking about or climbing stairs difficult?

FIG. 36

DEVICES AND METHODS FOR MONITORING PHYSIOLOGIC PARAMETERS

CROSS-REFERENCE TO RELATED APPLICATIONS

This application is a continuation of PCT/US2016/061993 filed Nov. 15, 2016, which claims the benefit of priority to U.S. Provisional Application No. 62/255,915 filed Nov. 16, 2015 and U.S. Provisional Application No. 62/264,734 filed Dec. 8, 2015 and U.S. Provisional Application No. 62/302,684 filed Mar. 2, 2016 and U.S. Provisional Application No. 62/331,263 filed May 3, 2016 and U.S. Provisional Application No. 62/402,244 filed Sep. 30, 2016, each of which is incorporated herein by reference in its entirety.

FIELD OF THE INVENTION

The present invention relates to the field of monitoring cardiac function.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Heart failure (HF) is the leading cause of hospitalization among adults over 65 years of age in the United States. In 2014, more than 5.1 million people in the United States were living with a diagnosis of HF, and as many as one in nine deaths each year can be attributed to complications stemming from this disease. Acute decompensation is a life-threatening consequence of HF that occurs when uncontrolled fluid retention in the thoracic cavity prevents the heart from maintaining adequate circulation. An important component of managing HF patients is maintaining an appropriate fluid volume by adjusting the patient's medications in response to his/her cardiac function. Fluid volume metrics, such as dyspnea, edema, and weight gain, can be monitored by patients at home as an indirect indicator of worsening cardiac function, but are highly non-specific and cannot predict decompensation risk with sufficient resolution to affect the hospitalization rate. Recent evidence has shown that directly monitoring cardiac function via an implantable sensor can provide clinicians with a remote monitoring tool to determine when medication adjustments can prevent decompensation and the need for hospitalization. However, the cost and invasive nature of these sensors severely restrict their potential for clinical adoption.

Various mechanisms have been employed to determine cardiac function and health. These include invasive technologies such as the Swan Ganz catheter and a pulmonary artery implant to less invasive technologies such as arterial waveform monitoring devices, and surface worn technologies such as bioimpedance monitors and noncontact technologies such as scales to monitor weight. The invasive technologies are more accurate but also more risky while the noninvasive technologies have less risk but are more cumbersome and typically less accurate. The presence of collected fluid, peripheral edema, ascites, pleural effusions and weight can also be used to monitor cardiac function in CHF patients, but these parameters are merely symptomatic surrogates with poor correlation to actual cardiac output.

What is needed is a simple, repeatable, accurate monitor of cardiac function and other physiologic parameters that allows consistent measurement of cardiac output in the clinic, hospital and/or home environment. The present invention provides an easy to use, home-based device and method for the tracking of cardiac output, stroke volume and cardiac function. The invention can also be used for monitoring mechanical phases of the cardiac cycle, which are useful for diagnosing structural issues such as heart valve pathologies.

SUMMARY OF THE INVENTION

The present invention is a non-invasive respiratory monitor that is capable of directly monitoring cardiac function in a remote setting. The respiratory monitor, or airway device/controller, detects minor variations in expiratory airflow pressure known as cardiogenic oscillations (COS), which are generated by changes in the pulmonary blood volume that correspond with the cardiac cycle. The strength, or magnitude, or variations in magnitude, of cardiac oscillations is a direct indicator of cardiac function and is directly correlated with stroke volume and inversely proportional to pulmonary artery pressure.

Minor, cyclic waveforms caused by cardiogenic oscillations, or cardiac pulses, can be detected in the bulk pressure and flow measurements of expiration and inspiration. The method and device of the present invention utilizes this ability to detect and isolate cardiac oscillations, or pulsations, within the sensed pressure profile in the airway of an animal or human. Pressure measured at around 100 Hz, or around 80 Hz to around 120 Hz, within the airway of a subject allows for excellent resolution of the pressure signal. When pressure in the airway is measured at this frequency, cardiogenic oscillations may be visible in the resulting pressure curve. These pulsations are best seen at end expiration, or during a breath hold, but can be seen throughout the breathing cycle. This result may be the result of the heart beating in close proximity to the lungs, which subsequently transmits the pressure fluctuations through the trachea to the mouth and nose. It may also be the result of pulmonary blood flow, which may slightly compress the lungs as the heart beats.

The magnitude of cardiac oscillations is indicated by the standard deviation, or variations, of the cardiac oscillation pressure waveform and is a direct indicator of cardiac function and is directly correlated with stroke volume and inversely proportional to pulmonary artery pressure. The cardiac performance of patients with heart failure is reduced when compared to that of healthy individuals, which will dampen the cardiac oscillation curve relative to healthy subjects.

In one embodiment of an airway device as described herein, the device may generally comprise a mouthpiece section and an opening section defining one or more airway lumens therethrough. The airway device may further comprise a first sensor in fluid communication with the one or more airway lumens and configured to detect an airway pressure when a user inhales or exhales through the one or more airway lumens, a second sensor positioned upon a hand-piece for contact against a portion of the user and configured to detect a physiological signal from the user, and a controller in communication with the first and second sensors, wherein the controller is programmed to correlate pressure oscillations in the airway pressure received from the first sensor with heartbeats received from the first sensor, the second sensor, or pressure data corresponding to a rough airway pressure In one embodiment of a method of correlating physiologic parameters, the method may generally comprise detecting via a first sensor an airway pressure of a user while inhaling or exhaling through one or more airway lumens of a respiration device having a mouthpiece section and an opening section, detecting via a second sensor positioned upon a hand-piece of the respiration device a physiological signal sensed from the user in contact with the second sensor, and correlating via a controller pressure oscillations in the airway pressure received from the first sensor with a timing of heartbeats received from the first sensor, the second sensor, or pressure data corresponding to a rough airway pressure.

The present invention senses pressure and/or flow within the airway by exposing the airway (via the patient's nose or mouth) to one or more pressure, flow, and/or other sensor(s). When the epiglottis is opened, this exposure to the airway allows pressure and/or flow sensors to detect small pulsations that occur during heart function. These fluctuations may also be detected with a sensitive enough sensor, when the epiglottis is closed. With an appropriately sensitive sensor sampling at a rapid frequency, waveforms can be seen in the airway corresponding to contractions, relaxation and valve openings in the heart. This phenomenon has been found to be repeatable and allows not only for tracking of heart and lung function and/or conditions (i.e. pulmonary edema, pleural effusions, congestive heart failure, aortic insufficiency, mitral, pulmonic, tricuspid insufficiency, etc.) but can be used to diagnose disease in patients using the airway device. Whereas ECG is used to monitor and diagnosis heart conditions based on the electrical signal being sent to the heart, the present invention provides additional information based on the actual mechanical function of the heart.

Preferably, the amplitude and/or area under the curves for pressure and/or flow data can be used to determine relative pulmonary blood flow, relative stroke volume, and/or relative pulmonary artery pressure. For example, as pulmonary blood flow increases, the amplitudes of the flow pulsations in the breath increase. Additional parameters, such as the slope of the pressure curve, changes in the curve or standard deviation of the curve can also be used to determine relative cardiac function. When tracked over time, these parameters provide noninvasive insights into the patient's changing cardiac health and can be used to adjust his/her care accordingly. This is particularly useful for people who are being monitored regularly for changes in their conditions, such as patients with heart failure. Patient pressure/flow curve data can also be compared to those of healthy or unhealthy patient populations to asses a particular patient's, or a group of patients', health In some embodiments, the patient is prompted by a controller to breathe into the device naturally for several cycles. This may be done automatically by a controller. Further, the airway device may be simply placed in the mouth and worn while going about activities of daily living to allow for natural sensing of respiratory rate, another powerful predictor and indicator of progressing illness. In some embodiments, the airway device/controller can calculate the rate of exhalation and capture cardiogenic oscillations at the same phase of breathing for each patient to allow for consistent measures of cardiac output and lung function. In other embodiments, the mean or median of the samples may be used as the representative value for that particular measurement. For example, the patient may breath regularly for 2, 5, or 10 minutes, during which the pressure, flow, and other signals are captured, and at the end the of the session values such as the average amplitude of the signal caused by cardiogenic oscillations may be reported. In this way intra-measurement variability is reduced and the signal-to-noise ratio is improved.

Further, in some embodiments, the patient may be prompted by a controller to inhale deeply and hold his/her breath (or, if used in conjunction with a ventilator, the ventilator can be paused at end inhalation, end exhalation, or elsewhere, either manually or, preferably, automatically with communication between airway device/controller and the ventilator or incorporation of airway device/controller into the ventilator) to see the impact of breathing on the pressure waveform. Variability in the respiratory pulse pressure waveform can be used to determine hydration status, as well as volume status. Dehydrated or hypovolemic patients will see a pulse pressure waveform that varies throughout the respiratory cycle due to the change in cardiac function with the changing thoracic pressures found with respiration. As fluid status is restored, this variability is reduced and lack of variability can provide a powerful indicator that fluid status has been restored. In addition to pulse pressure variability, heart rate variability may also be used to assess fluid status. Variability may be assessed on a continuous basis during natural or mechanical ventilation or may be assessed during a respirator pause to look for changes at end-inspiration and/or end-expiration over time to track variability. The ratio of end-inspiratory to end-expiratory pulse amplitude during respiration or with a breath hold may be determined. Variations in waveform peak-to-peak period and magnitude, in addition to other parameters, may be determined.

In some embodiments, the patient may be prompted by a controller to exhale against resistance, while leaving his/her throat open (i.e., leaving the glottis and/or epiglottis open). This is referred to as a "modified Valsalva maneuver" or MVM. The patient/user may be prompted to exhale within a specific pressure range and for a specific time period. For example, the user may be prompted to exhale at a pressure of 10 mm Hg (±0.5 mm Hg) for at least 5 seconds. "Exhaling" may include exhaling into a closed or open system. If the system is open, for example, with a resistance control orifice, the resistance control orifice must be small enough to allow the user to exhale at the given pressure for the given time frame. In other words, the vent can't allow more than a breath's air capacity to escape at the required MVM pressure. The user may be prompted by the controller, or instructed, to perform the MVM within the proper parameters (open throat, pressure, and time).

A respiratory pause may also be used to provide another determinant of cardiac output-change in end-tidal CO2 after a respirator pause. The use of respiratory pulse pressure waveform analysis in conjunction with the end tidal CO2 method may improve the accuracy of the results and make this method less susceptible to pulse pressure variability.

In addition, actual, or absolute, cardiac output can be determined without calibration using the airway device/controller. By combining the airway device/controller with spirometry or a ventilator, the volume of air in the lung can be accurately estimated. In addition, actual, or absolute, cardiac output can be determined using a CO2 sensor to determine end tidal CO2, as well as an air flow sensor and oxygen sensor. The calculations to determine cardiac output can be performed as described in "Noninvasive Monitoring Cardiac Output Using Partial CO2 Rebreathing" by Brian P. Young, M D, and Lewis L. Low, M D. A spirometer and/or ventilator may be stationary or ambulatory, or may be miniature and built into the mouthpiece itself.

In another embodiment, absolute stroke volume, cardiac output, and/or pulmonary artery pressure can be estimated by comparing the amplitude of the pressure or flow curves in the airway to the volume of air in the lungs and using correlation coefficients based on patient based variables such as their gender and height, in a similar manner to the way correlation coefficients can be use with pulse-transit-time to estimate blood pressure (see Gesche, Heiko, et al. "Continuous blood pressure measurement by using the pulse transit time: comparison to a cuff-based method." (2011)). In this manner, the present invention may be used to estimate the actual volume displaced in the lung by the cardiac pulse, which represents the true stroke volume. An ECG or pulse oximetry signal may be used to help determine the pulse transit time.

Furthermore, in the setting of low pulse pressure variability this technique can also be used to calculate the dead space in the lung. This can be done by comparing the cardiac pulse pressure waveform at end-inhalation and end-exhalation. If tidal volume is known (i.e. with spirometry or mechanical ventilation), then, assuming the cardiac pulse is a constant, one can calculate the dead space in the lung by looking at the magnitude of the cardiac pressure pulse and calculating the predicted amplitude of the cardiac pulse, measuring the actual amplitude of the cardiac pulse, and determining the dead space information from the difference between the two (due to the extra dead space being compressed also). Total lung volume may also be calculated by the application of a fixed amount of analyte or a small bolus of gas/air to the lung then calculating the resulting concentration of the analyte or the final pressure after delivery of the bolus of air (assuming a breath hold at end-inspiration).

Due to its ease of use and non-invasive nature, the present invention lends itself well to home healthcare monitoring. In a preferred embodiment, the airway device will be handheld or body worn (but does not need to be). The airway device may continuously or intermittently measure flow rates/volumes, pressure, temperature, and/or gas concentrations in the airway. Patient manipulations may be requested by the airway device/controller (i.e. "Breathe deep then hold your breath for 5 seconds") and the airway device/controller may be able to automatically or manually communicate the extracted information to the patient and/or healthcare provider, or with a mobile device, computer, server or other device. Alerts may be programmed into the airway device and/or controller, as well, to warn of impending issues or danger, or to guide the user through its use. By continuously sensing the pressure, the airway device/controller may also provide continuous feedback on the adequacy of the patient manipulations (i.e. "Slow down the speed of your breath") to optimize the patient manipulations for improved data capture. Alerts may be audible, visual, vibration, etc. Alerts may also be sent to a physician, monitor, hospital, EMR etc. Alerts may be transferred wirelessly to any device including a mobile device, computer, server, etc.

In temperature-sensing embodiments, the airway device/controller may sense inhaled and exhaled temperature and the controller, based on flow/heat exchange algorithms, reports the patient's temperature. Alternatively, the airway device/controller may report trends in temperature based on baseline data acquired when the patient was at a normal temperature. This deviation from baseline data can be utilized with any of the sensed parameters thereby allowing for the determination of a relative change in any of the parameters without knowing the actual value of any of the parameters.

In any of the home health, clinic or hospital embodiment of the airway device/controller of present invention, additional functionality may be incorporated, including temperature sensing, respiratory function monitoring (i.e. spirometry), acoustic monitoring (to track wheezing in asthmatics, etc.), detection of analytes and/or compounds in the breath (i.e. urea, markers of infection, O2, CO2, water vapor, etc.), detection of analytes in the saliva (since the device may be placed inside the mouth in some embodiments). Additional air sensors may include alcohol, and/or other drugs such as narcotics, marijuana, tobacco, etc.

In addition, physical sensors in contact with the body, for example the lips, fingers, hands, may include ECG sensors, pulse sensors, mucosal contact sensors, etc. When ECG sensors are in place, sampling of the pulsatile signals in the breath from the cardiogenic oscillations may be synchronized with the ECG signal in order to identify periodic signals, evaluate only the relevant portions of the signal and to reduce the amount of noise. For example, the magnitude of change in the pressure and/or flow signals during a set amount of time (such as 200 or 500 ms) may be the variable of interest that is tracked over time to monitor the cardiac health of the patient. A 2-lead ECG may also be used. The R wave, of the ECG signal may be used for synchronization. Pulse oximetry may also be used.

The amplitude of cardiac oscillations is directly affected by pulmonary blood flow (PBF) in a linear manner, and the amplitude of this cardiac oscillation peak is likely correlated to the pulmonary blood volume variation (PBVV), which is defined as the change in the pulmonary blood volume from systole to diastole. PBVV has previously been investigated as a metric of cardiac function during heart failure. The PBVV reflects an increase in capillary volume that impinges upon the compliant bronchiole network leading to the alveoli of the lung and generates high frequency peaks in airway pressure during systole phase of the cardiac cycle. These peaks of cardiac oscillations can be detected. PBVV is proportional to the stroke volume and both values decrease as the cardiac output declines during heart failure. PBVV is also inversely proportional to increases in vascular resistance coincident with heart failure, which restrict the ability of the pulmonary capillaries to expand into the pulmonary airways and contribute to pulmonary hypertension. Thus, the standard deviation of cardiac oscillations (SDCOS) is directly proportional to cardiac output and inversely proportional to pulmonary artery pressure (PAP):

$SDCOS \propto a*(-\Delta APAP)+b*\Delta PBF$ where a and b are constants representing compliance of the pulmonary arteries and bronchioles, respectively.

Pulmonary Arterial Compliance

Pulmonary Arterial Compliance (PAC) is related to Cardiac Heart Failure (CHF) and is a strong indicator of CHF. As the pulmonary artery becomes congested, PAP increases, as PAP increases, the pulmonary artery stretches. But, at higher pressures (above about 25 mmHg), the pulmonary artery becomes less able to stretch further which leads to increased pulse pressure within the pulmonary artery (pulmonary artery pulse pressure, or PAPP). As a result of the higher pressures within the pulmonary artery, more work is required from the right ventricle, and stroke volume (SV) is increased.

PAC can be calculated as SV/PAPP (mL/mmHg)

Pulmonary arterial compliance has been shown to be a strong indicator of cardiovascular death or complications.

As PAC decreases, the chance of cardiovascular complications or death increases. In addition, treatments for heart failure have been shown to increase the PAC. Currently, the only reliable way to measure PAC is with an invasive catheterization procedure.

Cardiogenic oscillations are generated by the cardiac pulsation in the pulmonary vasculature and are directly related to PAC. As heart failure worsens, stroke volume may decrease which leads to a decrease in the PAC amplitude. Also, PAP increases, the pulmonary artery stiffens, and PAPP increases, also leading to a decrease in the PAC amplitude. A decrease in PAC or PAC amplitude, is a strong indicator of worsening heart health. Amplitude in this instance refers to peak-to-peak amplitude of the curve.

In one use case example, the airway device/controller can be used to track a patient with congestive heart failure. If the patient using the airway device/controller is found to have decreased stoke volume or increased pulmonary artery pressure (via the pressure and/or flow sensors), decreased lung volume and/or decreased respiratory compliance due to fluid accumulation in the pleura and/or pulmonary spaces (via spirometer or pressure sensor) and/or enlargement of the heart, increased pathologic lung sounds (via the acoustic sensor/microphone), increased end-tidal CO2 and/or an increased respiratory rate (via the pressure sensor or spirometer) then the healthcare provider or patient may be alerted that their condition is worsening.

In the home healthcare embodiment, the patient may then be sent home with a networked device (or return to the clinic) for repeat measurements. In the instance where this device is used in combination with daily weighings on a networked scale, the airway device/controller may communicate with an existing network provided by the scale or other in-home patient monitoring device, or any network, to alert the user and/or healthcare provider. In this way, the patient's cardiac health can be monitored remotely and noninvasively. This technique may also be used in lieu of radiographic examination to look for pneumo- or hemothorax following a procedure. Tension pneumothorax and detection of any other lung pathology may be accomplished with this technology, as well, in the hospital, office, or home setting.

In an alternative embodiment, the airway device/controller may record noises directly within the respiratory tract. In this embodiment, the airway device/controller may incorporate a disposable or reusable microphone attached to the airway device, (or alternatively, to a ventilator, vent tube or endotracheal tube). The microphone can track respiratory sounds and rapidly report the onset of respiratory distress, pneumonia, rales, rhonchi or other changes in lungs sounds. In its preferred embodiment the airway device/controller may incorporate noise cancellation functions. In one such embodiment, two microphones may be used within the airway device with one microphone facing the airway and the other microphone in a similar position within the airway device but sealed off from the airway. The signal from the sealed off microphone may then be subtracted from the microphone open to the airway thereby cancelling out ambient noise and allowing resolution of the physiologic sounds (cardiac, respiratory, gastrointestinal, etc.).

In some embodiments, the airway device/controller could be used in the placement and/or continuous monitoring of an endotracheal tube (ET). ET placement is related to causes of infection in ventilator-acquired pneumonia patients: poor placement can lead to pooling of fluid and, within the fluid, bacterial colonization can occur which then can migrate through the ET or around the cuff of the ET and into the lungs. Pooling of fluid and/or changes in respiratory flow/pressure can be monitored to obtain an early onset indication of infection. Bacteria may also be detected through sensors on the device.

In yet another embodiment, the airway device/controller can detect pathologic behavior of the heart valves. For example, when used in combination with an ECG, the expected mechanical heart behavior and timing of the cardiac cycle is known. By comparing the electrical and mechanical signals, improper mechanical function can be detected, such as the timing of the contraction of the atria or ventricles and opening or closing of the heart valves. Furthermore, the intensity and timing of these signals can also be used to diagnosis pathologies—for example, whether certain phases of the cardiac cycle are prolonged or incomplete, such as with mitral valve regurgitation. This information may be used alone or in combination with the sound information described above or with any other technique for diagnosing heart murmurs in order to better understand the underlying heart function or dysfunction.

This and any of the embodiments described herein may be utilized in a continuous or intermittent manner. The airway device may be designed to be worn by the user or require additional equipment to function and may be applied to the nose and/or mouth or applied directly to an endotracheal tube. The airway device/controller and any or all of its functions may be used in any setting including: the home, office, clinic, hospital ward, ASC or ICU.

The airway device/controller may be used to monitor chronic conditions and/or detect acute conditions including: COPD, asthma, CHF, cancer, stroke, pulmonary embolism, and any other condition that could have an impact on respiratory rate, temperature, stroke volume, heart rate, tidal volume, lung sounds, heart sounds, GI sounds, pO2, pCO2, pH, or any other of the monitored parameters.

The airway device may incorporate a controller to analyze the signals from the various sensors. Alternatively, all, or part, of a controller may exist separately from the airway device and communicate with the airway device either wirelessly (via internet, intranet, WAN, LAN or other network, or it may be local via Bluetooth, Wi-Fi, etc.) or wired. If the connection is wired, it may be continuous or intermittent. For example, the data from the airway device may be periodically transmitted via a USB connection or other type of connection after data has been collected. A wireless connection may also be continuous or intermittent. The controller may be, or communicate with, one or more mobile devices, computers, servers, etc.

BRIEF DESCRIPTION OF THE DRAWINGS

FIG. 9 shows an embodiment of the airway device used wirelessly with a controller in the form of a smart phone.

FIGS. 21A-B show embodiments of the airway device/controller which include a hand-piece.

FIGS. 26A and 26B show 2 embodiments of the mouthpiece area of the airway device.

FIGS. 35 and 36 show example screens of a survey.

DETAILED DESCRIPTION OF THE INVENTION

Figure 1:
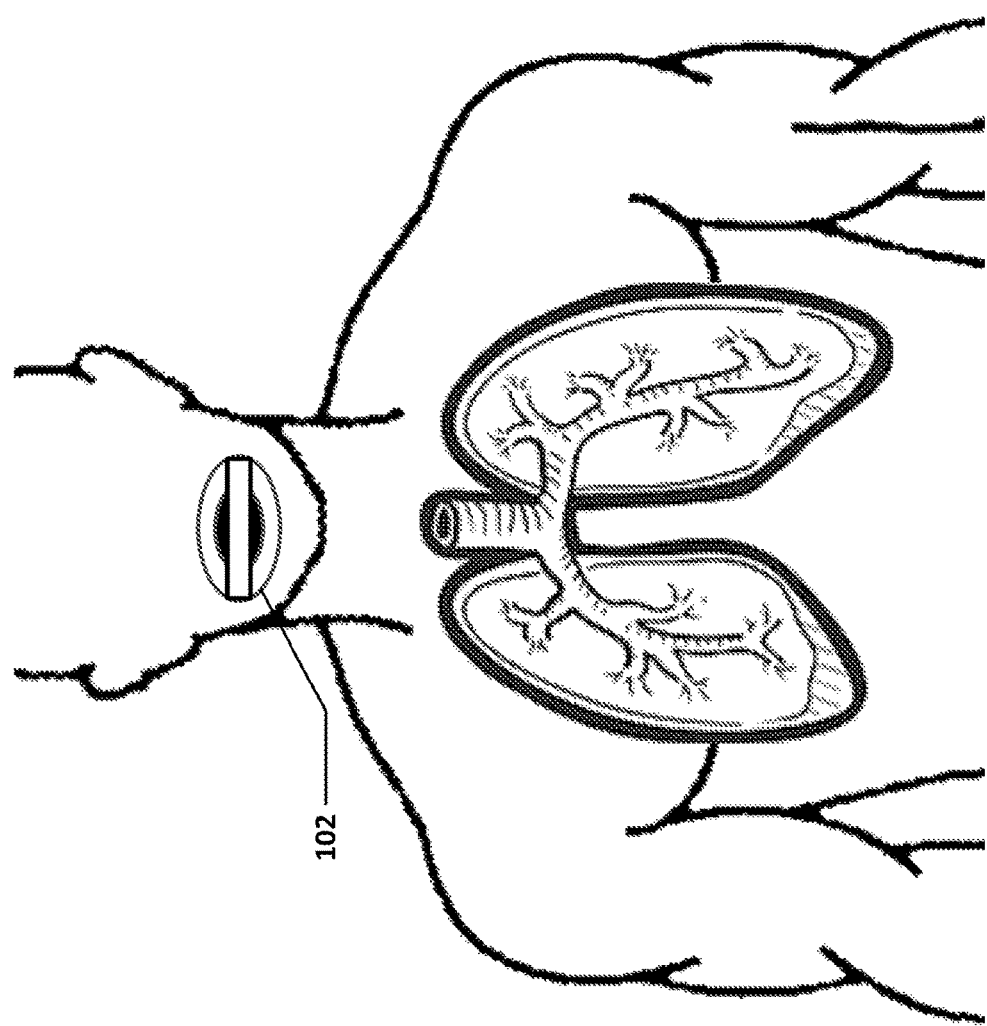
FIG. 1 shows one embodiment of the airway device/controller.

FIG. 1 shows an embodiment of the airway device worn in the mouth of a patient. One of the advantages of a portable embodiment, such as this one, is that it can be worn by a subject that is not only awake and not intubated, but upright and active. In other words, the use of the airway device is not limited to patients on a ventilator, CPAP, or other stationary medical device. The airway device/controller may be used on a patient/user with no additional ventilation support, or airway pressure support. Said another way, the airway device/controller may be used on a patient without a ventilator or CPAP machine or additional flow source, or any sort of artificial ventilation or airway pressure support. The airway device/controller may be used by patients/users who are breathing naturally or normally, or may be used in a "prompt mode", where the controller prompts the user to do something other than breathe naturally. For example, the controller may prompt the user to hold his/her breath, hold his/her breath after inhalation, hold his/her breath after exhalation, hold his/her breath "now", perform the MVM at a given pressure for a certain period of time, etc.

The airway device 102 contains one or more sensors which can measure and/or calculate airway pressure, airway flow, temperature, sounds, respiratory rate, stroke volume, heart rate, tidal volume, lung sounds, heart sounds, GI sounds, pO2, pCO2, pH, ECG, pulse rate, pulse pressure, spirometry, analytes and/or compounds in the breath (i.e. urea, markers of infection, O2, CO2, urea, water vapor, alcohol, drugs, etc.) or analytes and/or compounds in the saliva, such as glucose, etc.

A controller is either incorporated into the airway device or a separate device which communicates with the airway device either wirelessly or via a wired connection. The controller may be incorporated into a ventilator, a CPAP, a stand-alone device or incorporated into, or in communication with, a computer and/or smartphone.

In a preferred embodiment, the controller is incorporated into a smartphone which communicates wirelessly with the airway device, either on a continuous or intermittent basis. Data transferred from the controller may also be transmitted to/from a remote server, for example, via the internet or an intranet. Data from the controller may also be anonymized. Anonymized data may be aggregated across patients for trends analysis. Data collected may include metadata such as patient ID, timestamp, patient medical history, such as weight, medications, etc. Use of the term "airway device" herein may include a controller component.

The airway device may have a portion within the mouth or be completely external. It may also be over the nose either instead of, or in addition to, the mouth. The airway device may purposefully block the nose. The airway device may also be incorporated into an endotracheal tube.

Figure 2:
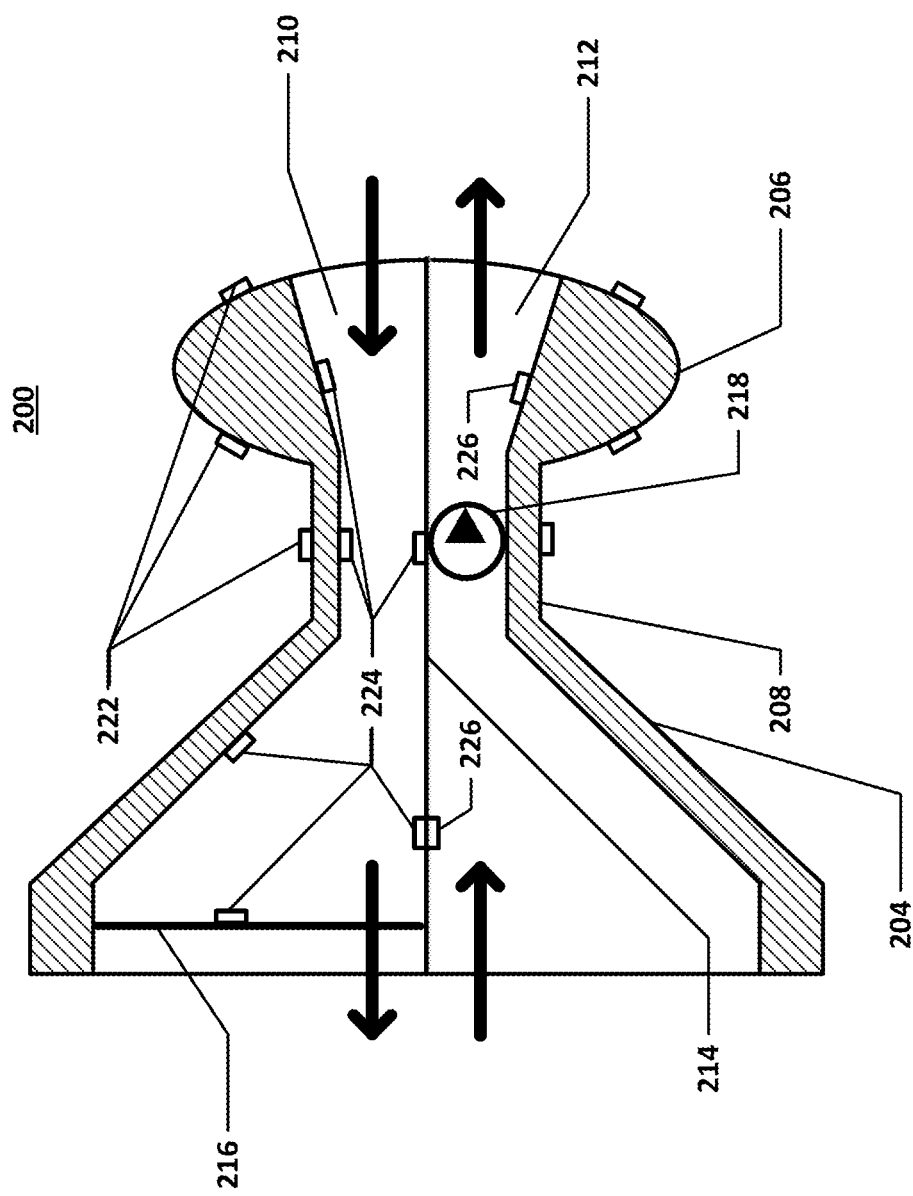
FIG. 2 shows an embodiment of the airway device/controller.

FIG. 2 shows a detailed view of an embodiment of airway device 200. This embodiment includes external opening section 204, mouthpiece section 206 and neck section 208. The mouthpiece device in this embodiment includes at least two airway lumens, exhalation airway lumen 210 and inhalation airway lumen 212. In this embodiment, the two lumens are separated by divider 214. Alternatively, only one lumen may be present, for example, only an exhalation lumen.

Gas outflow vent 216, in the exhalation airway lumen, may include a spirometry function. The vent may also maintain or cause to be maintained a slight positive pressure so that the airway of the subject remains open during breathing, which aids in the ability to sense certain parameters.

The air inflow, or inhalation airway lumen, and/or the exhalation airway lumen, may include one-way 218 valve to help direct exhaled air through the exhalation airway lumen during breathing.

Sensors 222, 224, and 226 may sense any of the parameters listed herewithin. Sensors may be placed in the exhalation airway lumen 210, the inhalation airway lumen 212, or on the outside of the airway device. Sensors 222 on the outside of the device will generally be for contact sensing with the mucosa and/or the lips, such as ECG sensors.

Sensors 224 in the exhalation airway lumen may measure parameters associated with exhaled air, including pressure, flow, sounds, O2, CO2, urea, water vapor, alcohol, drugs, etc. Sensors 226 in the inhalation airway lumen may measure parameters associated with inhaled air, including O2, CO2, urea, water vapor, alcohol, drugs, etc.

Generally, the sensors can be placed anywhere along the length of the airway device, but there may be advantages to certain locations for certain types of sensors. For example, sensors for temperature, water vapor, alcohol, drugs etc. measured in exhaled air, would likely be better placed closer to the subject.

Flow and/or pressure sensors can be placed anywhere along the length of the airway device, but there may be an advantage to placing these sensors in a narrow and/or constant diameter section of the airway device such as within neck 208. A sensor or sensors may also be placed on gas outflow vent 216. Sensors may also be remote. For example, a pressure sensor, for example a pressure transducer, may be in fluid communication with the mouthpiece via a tube with an inner lumen.

A single use barrier may be used to cover mouthpiece section 206 to maintain sterility of the airway device. Alternatively, a disposable mouthpiece section may be attached to the airway device and removed after use. A heat-moisture exchanger may be used to prevent humidity from the breath entering into the device. Alternatively, the airway device may be sterilizeable or disposable.

Airway device 202 may incorporate hardware and/or software to either act as a controller, or communicate with a controller. The airway device may also act as a "partial controller", where some of the controller activities take place within the airway device, and some take place within a separate controller device.

Airway device may be made out of any suitable material or materials, including polymer, metal, or any other material or any combination of materials. Airway device is preferably relatively light and portable.

Flow/pressure sensors may include orifice plates, pressure transducers, cone devices, Pitot tubes, Venturi tubes, flow nozzles, Fleisch or Lilly type pneumotachometers, or any other suitable technology. Sensor resolution is generally high. Pressure sensor sensitivity may around +/−0.5 mmHg. Pressure sensor sensitivity may around +/−1 mmHg. Pressure sensor sensitivity may around +/−2 mmHg. Alternatively, pressure sensor sensitivity may around +/−10 mmHg. Alternatively, pressure sensor sensitivity may around +/−20 mmHg.

Figure 3:
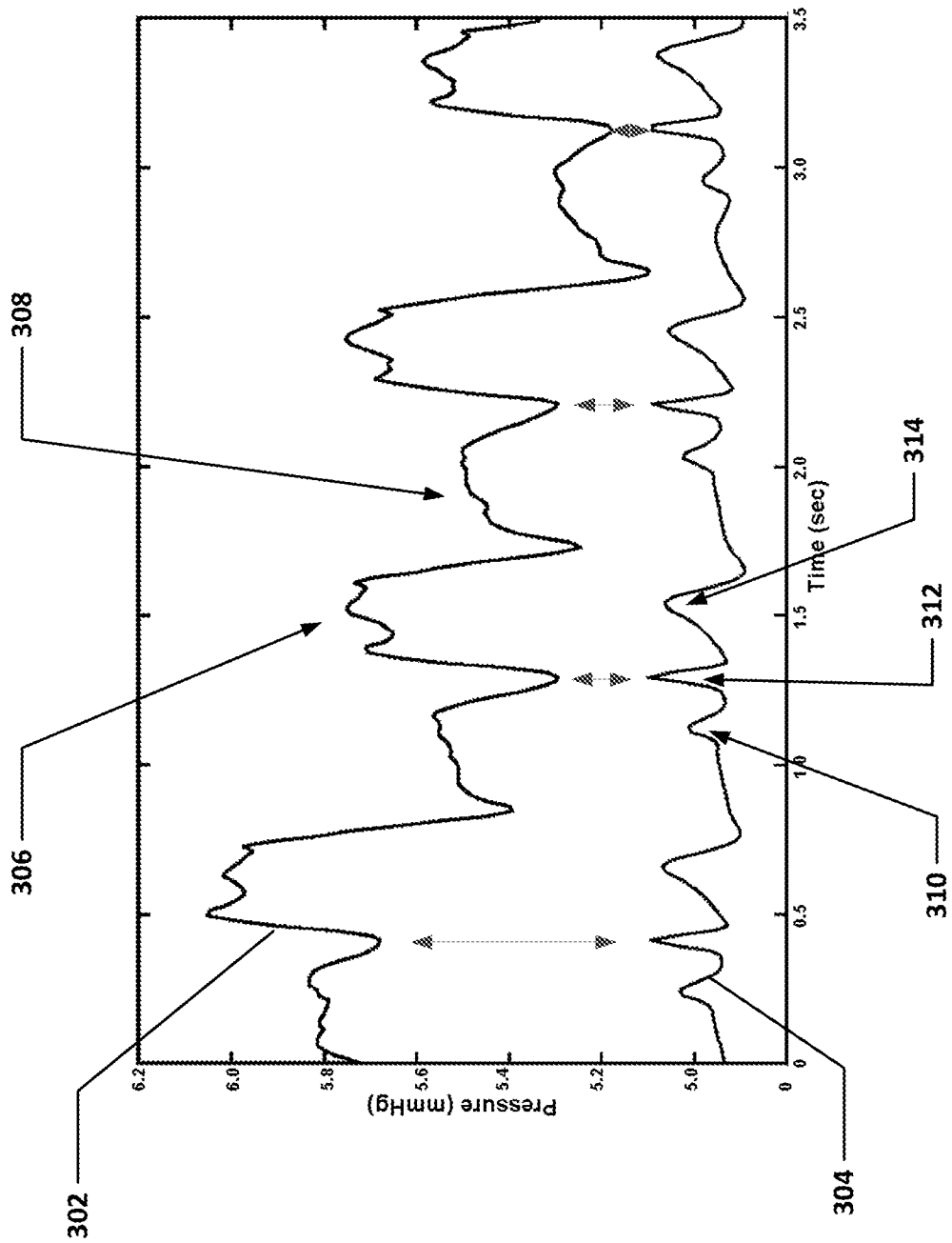
FIG. 3 is a graph showing an ECG overlaid on airway pressure data.

FIG. 3 shows a graph of an ECG along with simultaneously measured airway pressure data. ECG data 304 is shown below airway pressure data 302. Within the airway pressure, systolic pulse data 306 and diastolic pulse data 308 are clearly visible. Within the 3-lead ECG data, P wave 310, QRS complex 312, and T wave 314 are all visible. The double headed arrow lines show where the QRS complex peak lines up with the valleys of the pressure data.

Figure 4:
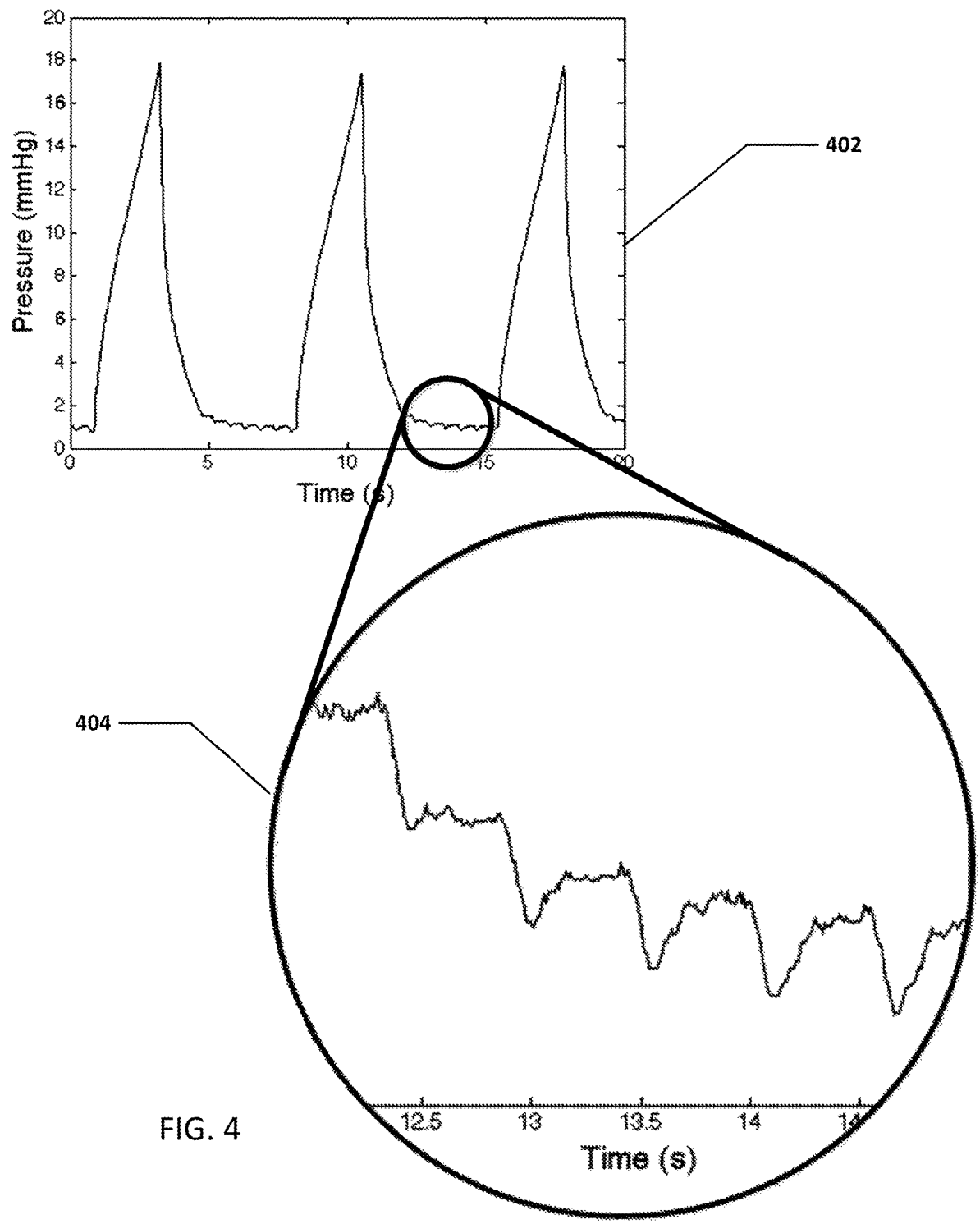
FIG. 4 is a graph showing pressure data from the ventilation tube of an animal.

FIG. 4 shows a detailed view of the pressure data between respirations shown in graph 402. Cardiogenic oscillations can be seen in detailed view 404 of pressure vs. time. The amplitude or area under the curve for these pulses can be used as an indicator of relative cardiac output and/or pulmonary artery pressure. Not shown but also useful in the same manner are cardiogenic oscillations in the flow signal.

Figure 5:
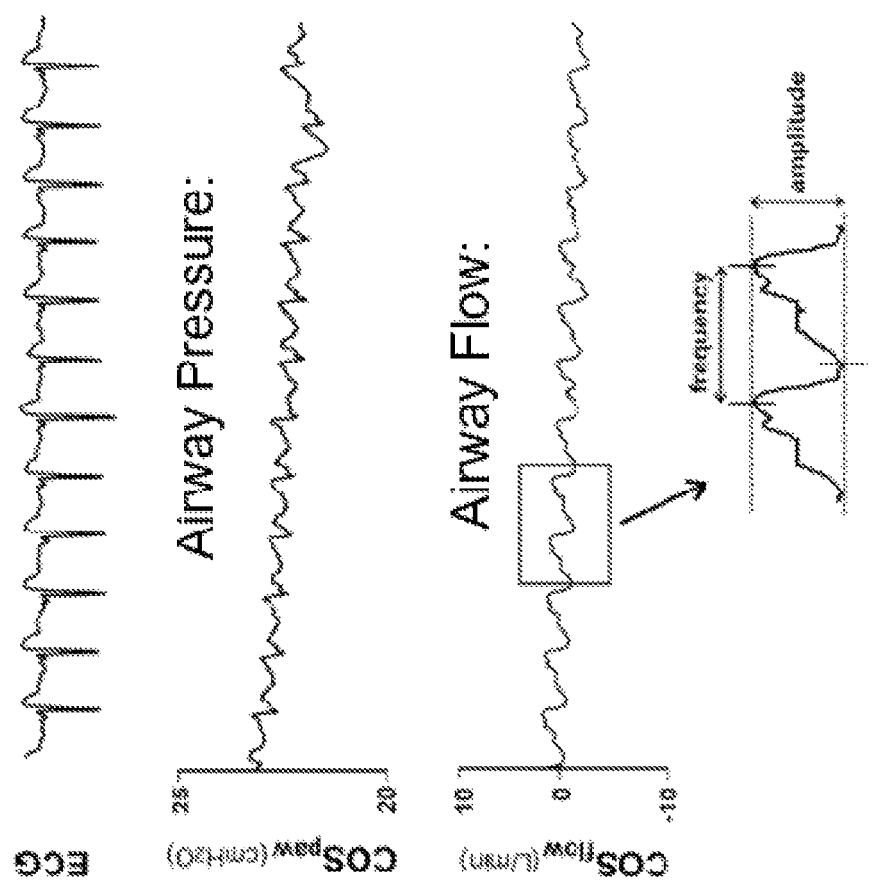
FIG. 5 shows a graph of the ECG curve as well as corresponding cardiogenic oscillations waveforms.

FIG. 5 shows a graph of the ECG curve, the cardiogenic oscillations waveform generated using data from pressure sensor(s), and the cardiogenic oscillations waveform generated using data from flow sensor(s). Also shown are the amplitude and the frequency of a cardiogenic oscillations waveform.

Figure 6:
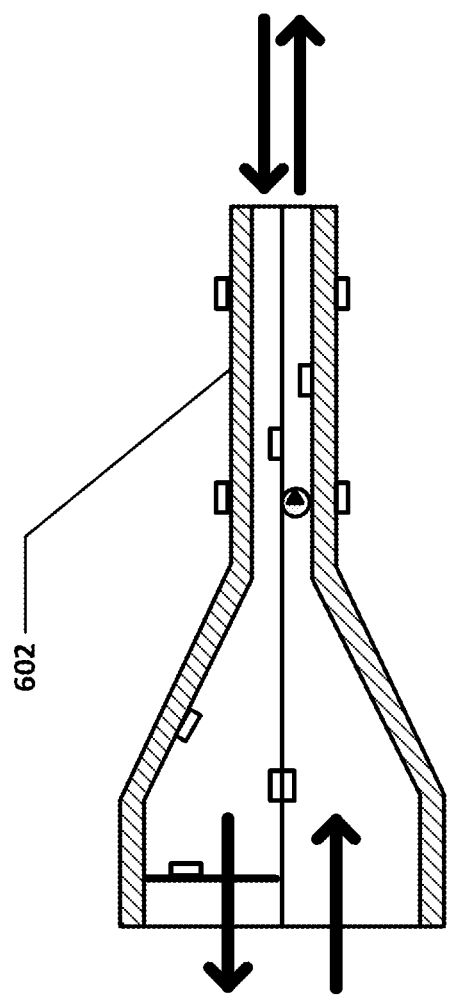
FIG. 6 shows an embodiment of the airway device/controller

FIG. 6 shows another embodiment of the airway device. The neck portion 602 is extended so that it also serves as the mouthpiece portion, which is more straw-like than the previously shown embodiment.

Figure 7:
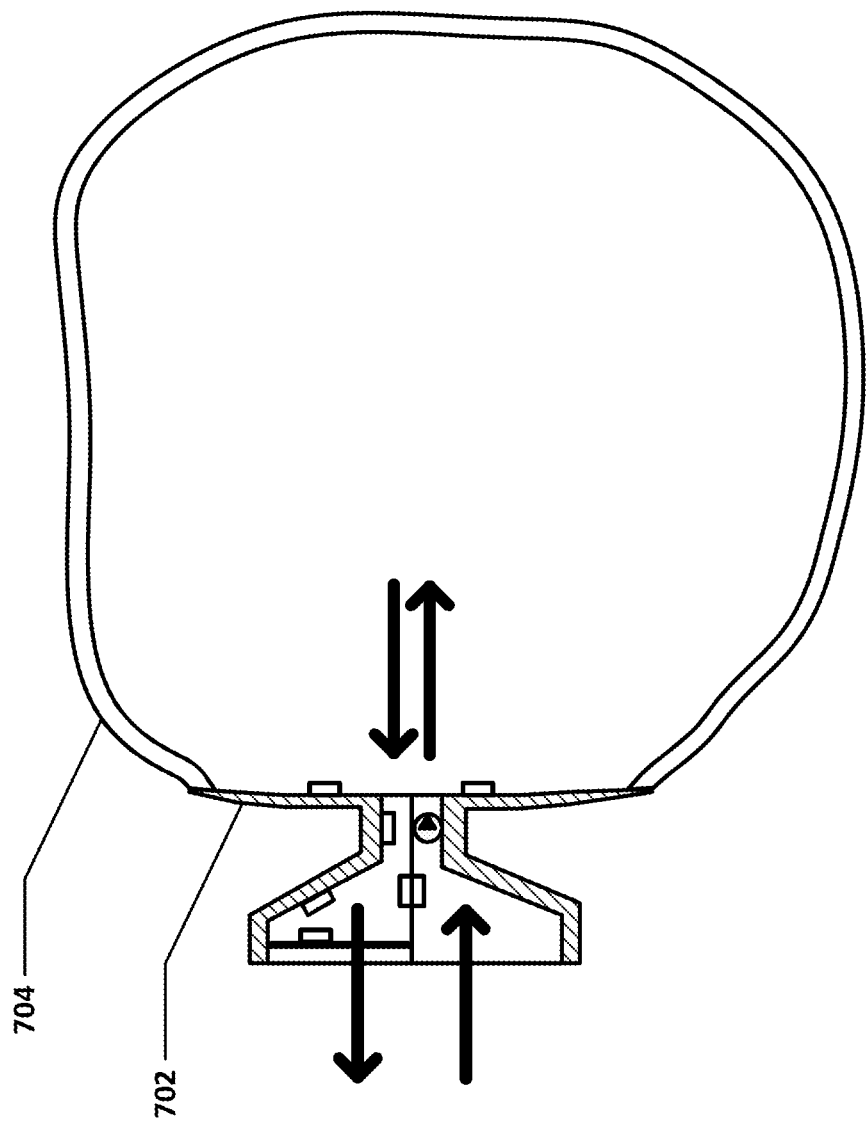
FIG. 7 shows an embodiment of the airway device/controller

FIG. 7 shows another embodiment of the airway device. Mouthpiece area 702 is flat and designed to go over the lips/mouth. Strap 704 may hold the device on the face of the subject.

Figure 8:
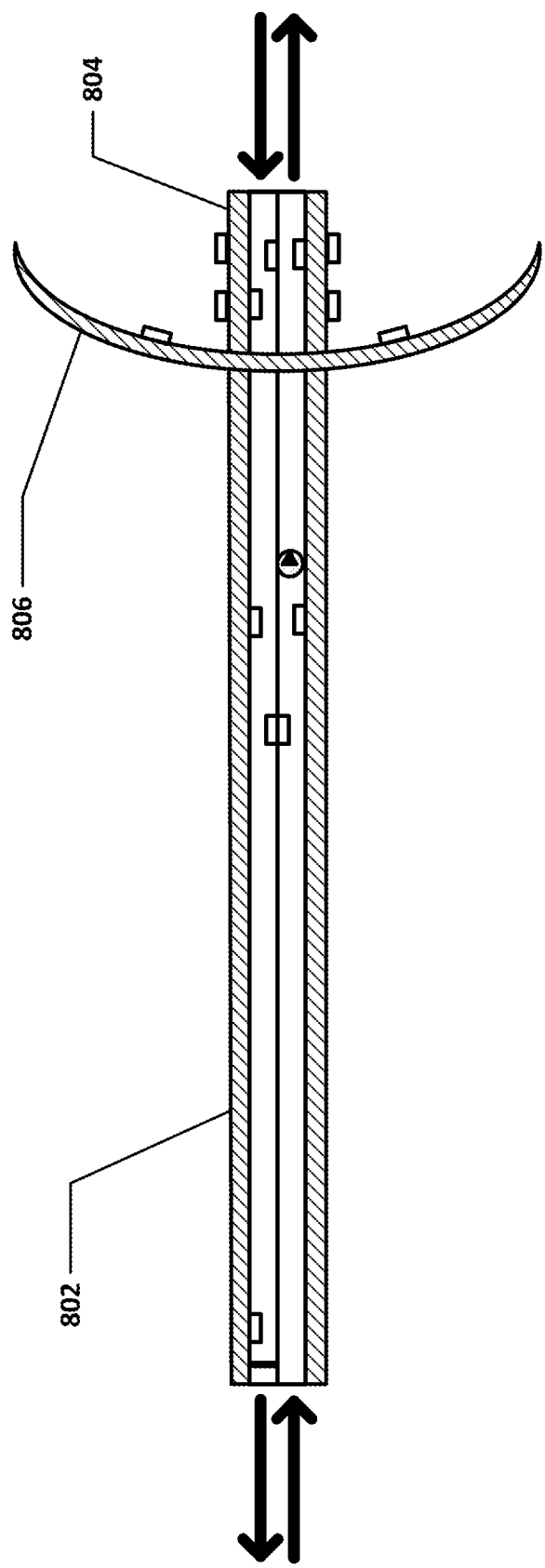
FIG. 8 shows an embodiment of the airway device/controller

FIG. 8 shows another embodiment of the airway device. External opening section 802 of this embodiment is elongated and more narrow than previously shown embodiments. Section 802 may be flexible, as in flexible tubing, or may be rigid, or may be partially flexible and partially rigid. Mouthpiece section 804 may include mouth shield 806 to help keep the device in place. The various sensors and/or valves may be anywhere along the length of this embodiment.

FIG. 9 shows an embodiment of the airway device and controller where the controller is separate from, and may be remote to, at least in part, the airway device. In this embodiment, controller 904 is a smart phone and communicates wirelessly with airway device 902, which may include a wireless data transmitter.

Figure 10:
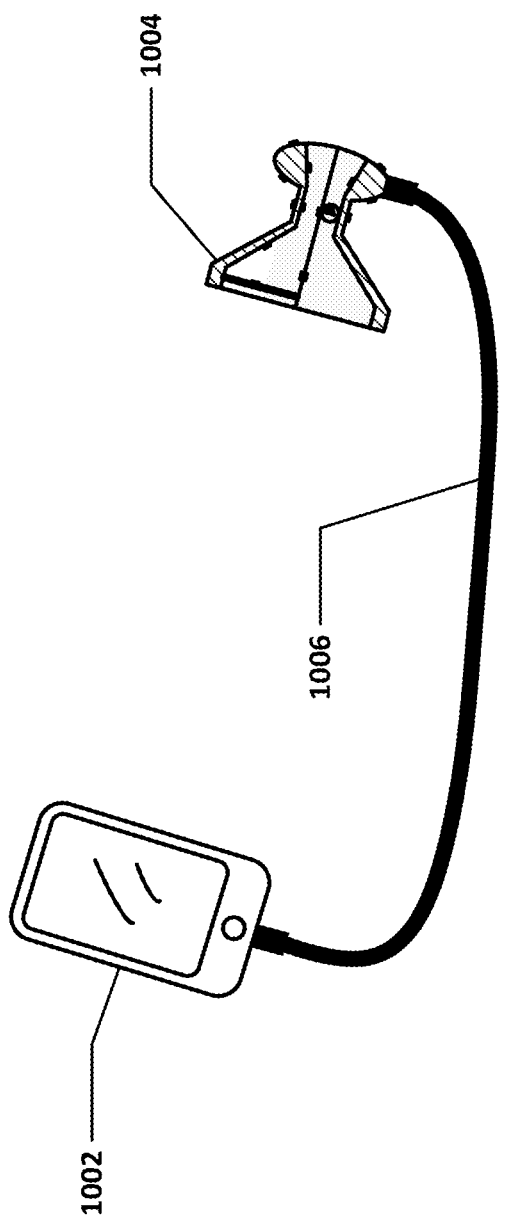
FIG. 10 shows an embodiment of the airway device connected to a controller in the form of a smart phone using a wired connection.

FIG. 10 shows an embodiment of the airway device and controller where the controller is separate, at least in part, from the airway device. In this embodiment, controller 1002 is a smart phone and communicates with airway device 1004 via a "wire" or cable 1006, for example, a USB cable. In this embodiment data may be collected and stored in airway device 1004 and periodically uploaded to controller 1002 via the cable. Alternatively, data may be stored, at least in part, in the controller.

The controller, whether it is separate from the airway device, or incorporated into the airway device, or some functions are located in the airway device and some located separately, may function as follows. The controller collects the data from the various sensors and analyzes them to determine cardiac output, stroke volume and/or cardiac function and/or other parameters. In addition, the controller may prompt the subject to help obtain the data from the sensors. For example, the controller may prompt the subject to hold his/her breath. The breath holding prompt may happen at certain phases of the breathing cycle, such as before or after inhalation and/or exhalation. The controller may prompt the subject to breath at a certain rate or to inhale, exhale, or hold his/her breath for a certain time period, or within a certain goal pressure range. Indicators may be present on the controller and/or the airway device to help the subject time certain activities, or achieve certain breathing goals, such as exhale pressure. For example, the controller may prompt the subject to hold his/her breath until a light on the controller and/or airway device turns green, or until an auditory signal is heard.

The controller may also determine whether the data it is collecting is adequate for analysis. For example, if the subject's airway is closing between breaths, or during exhalation, the data may be more difficult to analyze. The controller can sense when this is happening either by the pressure/flow profile or other parameters and can prompt the subject to adjust his/her breathing. For example, the controller may prompt the subject to breath more slowly, or to sit still. In addition, the controller may change the positive pressure of the airway device to help keep the airway open. Some possible prompts that the controller may provide to the subject are:

hold your breath for x seconds
hold your breath until the indicator does x
Breath normally until the indicator does x
exhale at a consistent pressure as shown on indicator
exhale at a consistent pressure as shown on indicator for x seconds (or until indicator says x seconds has elapsed)
exhale with throat open at a consistent pressure as shown on indicator for x seconds
perform the MVM for x seconds
exhale and then hold breath
inhale and then hold breath
breath normally
breath more slowly
Breath more quickly
Breath in slowly
Breath out slowly
Breath in quickly
Breath out quickly
testing is complete
begin exercising
end exercise Other prompts are also possible. The prompts may change depending on the data being collected. For example, if the controller determines that the airway is closing between breaths, during breathing, or during exhalation, the prompts may tell the subject to breathe differently, or the controller may cause the airway device to apply positive pressure to the airway. In addition, the user may be prompted at certain time(s) of the day to use the device, so that the device is used at the same time each day. For example, the device may prompt the user to use the device upon waking.

Other parameters that may be considered in determining whether the subject's breathing is optimal for data collection include: variability of peak-to-peak period and magnitude, waveform shape, etc.

The controller may analyze the data from the sensors to determine other conditions, including COPD, asthma, CHF, cancer, stroke, pulmonary embolism, dyspnea, paroxysmal, nocturnal dyspnea, emphysema, and any other condition that could have an impact on respiratory rate, temperature, stroke volume, heart rate, tidal volume, lung sounds, heart sounds, GI sounds, pO2, pCO2, pH, alcohol, urea, drugs, or any other of the monitored parameters.

Vagal tone/vasovagal syndrome may also be determined using the present invention. Slight changes in heart beat parameters, including amplitude, rate, waveform shape, etc., at different stages of the breathing cycle can be measured and vagal tone determined. For example, if the heart rate increases during inhalation, this may indicate a high vagal tone.

Example of Data Processing System

Figure 11:
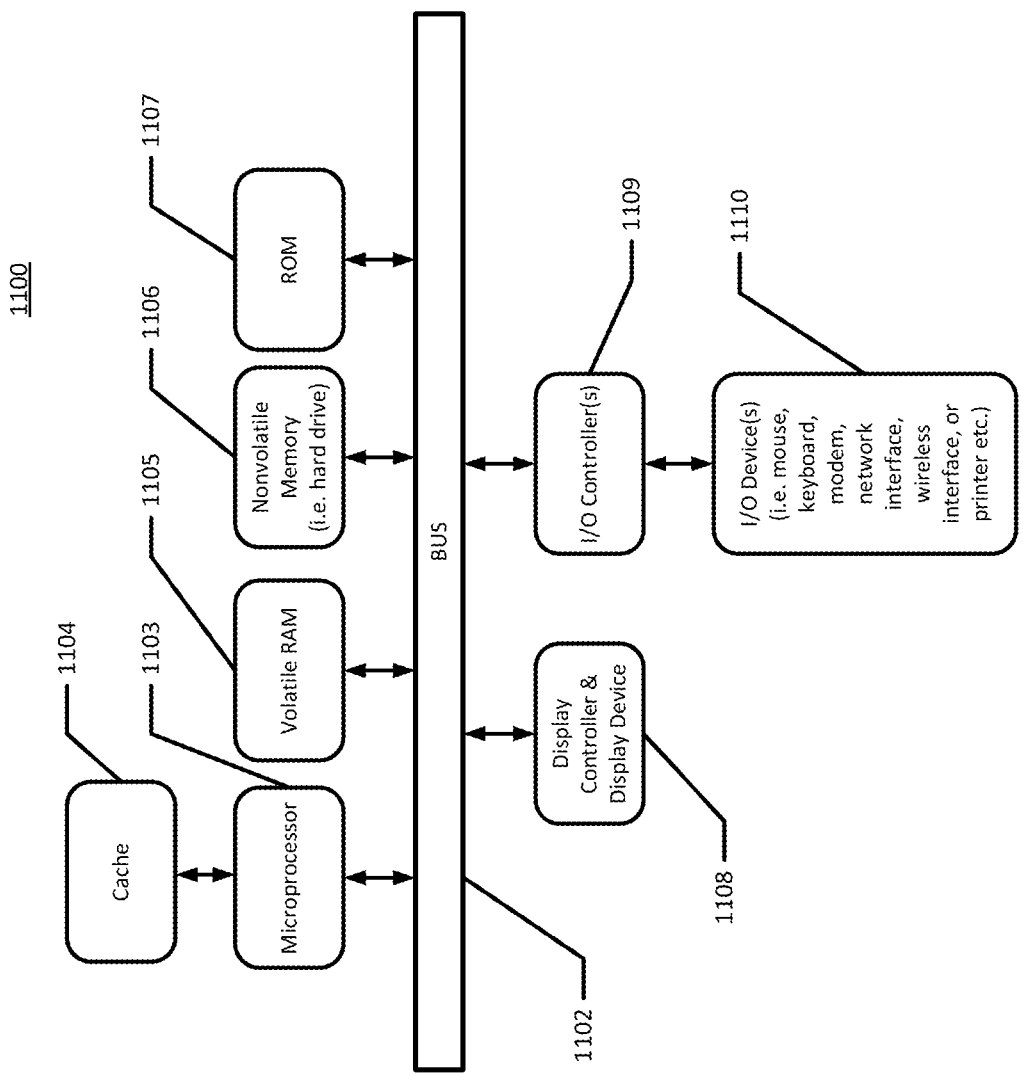
FIG. 11 is a block diagram of a data processing system, which may be used with any embodiments of the invention.

FIG. 11 is a block diagram of a data processing system, which may be used with any embodiment of the invention. For example, the system 1100 may be used as part of a controller, server, mobile device, hand piece, computer, tablet, etc. Note that while FIG. 11 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 11, the computer system 1100, which is a form of a data processing system, includes a bus or interconnect 1102 which is coupled to one or more microprocessors 1103 and a ROM 1107, a volatile RAM 1105, and a non-volatile memory 1106. The microprocessor 1103 is coupled to cache memory 1104. The bus 1102 interconnects these various components together and also interconnects these components 1103, 1107, 1105, and 1106 to a display controller and display device 1108, as well as to input/output (I/O) devices 1110, which may be mice, keyboards, modems, network interfaces, printers, and other devices which are well-known in the art.

Typically, the input/output devices 1110 are coupled to the system through input/output controllers 1109. The volatile RAM 1105 is typically implemented as dynamic RAM (DRAM) which requires power continuously in order to refresh or maintain the data in the memory. The non-volatile memory 1106 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 11 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1102 may include one or more buses connected to each other through various bridges, controllers, and/or adapters, as is well-known in the art. In one embodiment, the I/O controller 1109 includes a USB (Universal Serial Bus) adapter for controlling USB peripherals. Alternatively, I/O controller 1109 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the figures herein may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Figure 12:
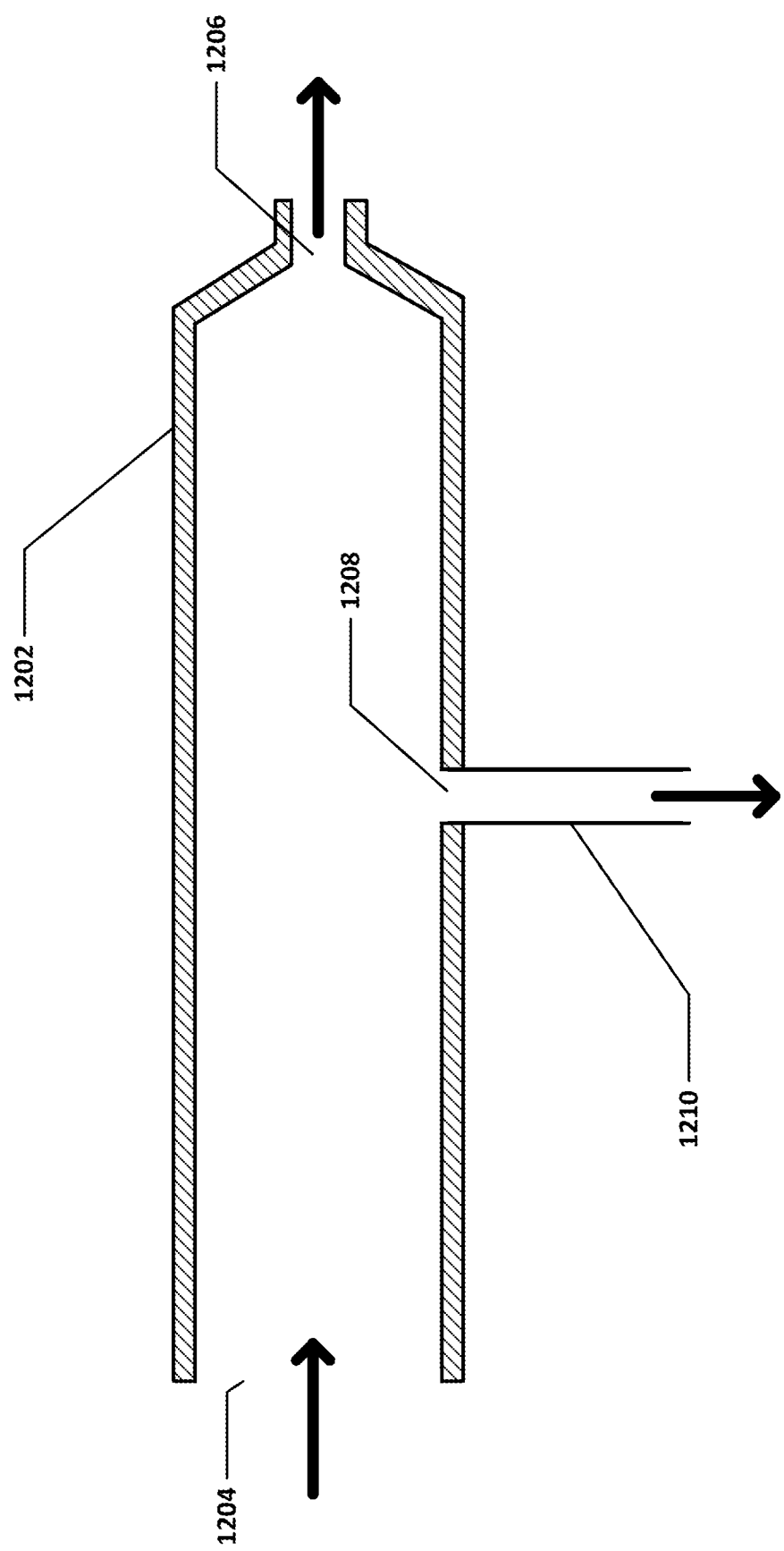
FIG. 12 shows an embodiment of a mouthpiece which includes a restrictor.

FIG. 12 shows an embodiment of an airway device which includes a restrictor. The restrictor helps reduce turbulent air flow within the airway device. Airway device 1202 in this embodiment has mouth opening 1204, which is larger than restrictor 1206. Restrictor 1206 is open to ambient air. As the user exhales into the airway device, restrictor 1206 restricts the airflow which increases the laminar nature of the air flow within the airway device. In this embodiment, as the user breathes through opening 1204, some air exits restrictor 1206, however some air, preferably air which is predominantly flowing in a laminar manner, exits sampling exit or lumen 1208. Sampling exit 1208 may connect directly to a pressure, or other, sensor, or it may connect to a pressure sensor or other sensor via connector 1210, which may be a flexible or rigid tube. The purpose of restrictor 1206 is to reduce turbulence in the air flow within the airway device so that the air exiting sampling exit 1208 is as laminar as possible. Note that this figure is showing an exhalation lumen only. A separate inhalation lumen may be incorporated into the device and/or the subject may be asked to inhale separately, either through his/her nose, or by removing the device from his/her mouth. Alternatively, the patient may also use the exhalation lumen for inhalation.

Figure 13:
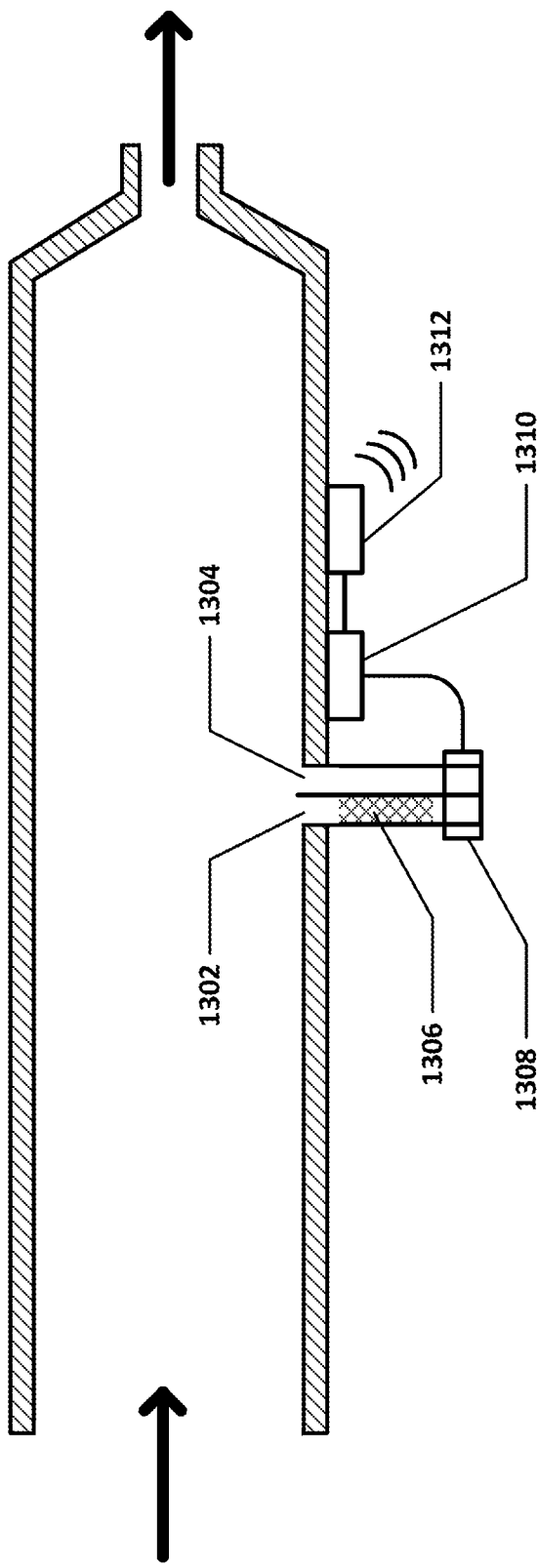
FIG. 13 shows an embodiment of a mouthpiece which incorporates a mechanical filter.

FIG. 13 shows an embodiment of an airway device which incorporates a mechanical filter. In this embodiment there are at least two sampling lumens, 1302 and 1304. One of the sampling lumen includes mechanical high pass filter 1306. The pressure sensor in this embodiment is a differential pressure sensor. Differential pressure sensor 1308 is in fluid communication with at least two sampling lumens or inputs, and compares the pressure reading between the two lumens. This configuration produces a cleaner pressure signal for analysis by circuit board 1310 by filtering out the pressure from the breaths and leaving those from the cardiogenic oscillations. Circuit board 1310 may be incorporated into the airway device or may be separate, for example on a separate controller, and communicated with either wirelessly or via wire. In this embodiment, the circuit board is incorporated into the airway device and communicates with a controller via wireless transmitter 1312. In this embodiment, circuit board 1310 and wireless transmitter 1312 may be considered to be part of the controller as well, for purposes of defining the controller. Filter 1306 may be made out of any suitable material including foam or any membrane that is semi-permeable to air. Note that this figure is showing an exhalation lumen only. A separate inhalation lumen may be incorporated into the device and/or the subject may be asked to inhale separately, either through his/her nose, or by removing the device from his/her mouth. Alternatively, the patient may also use the exhalation lumen for inhalation.

The mechanical high-pass filter isolates the higher frequency cardiac oscillation signal from the lower frequency pressure signal associated with natural breathing. This filter may employ a partially-impermeable barrier between differential sensing and reference inputs. The high-frequency cardiac oscillation signal is seen by the sensing input, whereas the pressure changes due to breathing are low frequency enough to equilibrate across the membrane and are detected at both inputs. By breathing into the device with a slight expiratory pause, or using the MVM, the cardiogenic oscillation signal can be reliably captured. Some embodiments may incorporate an additional, less sensitive, pressure sensor to monitor the entire breathing cycle and provide feedback to the patient about the size and frequency of the breaths, improving repeatability between measurements.

Figure 14:
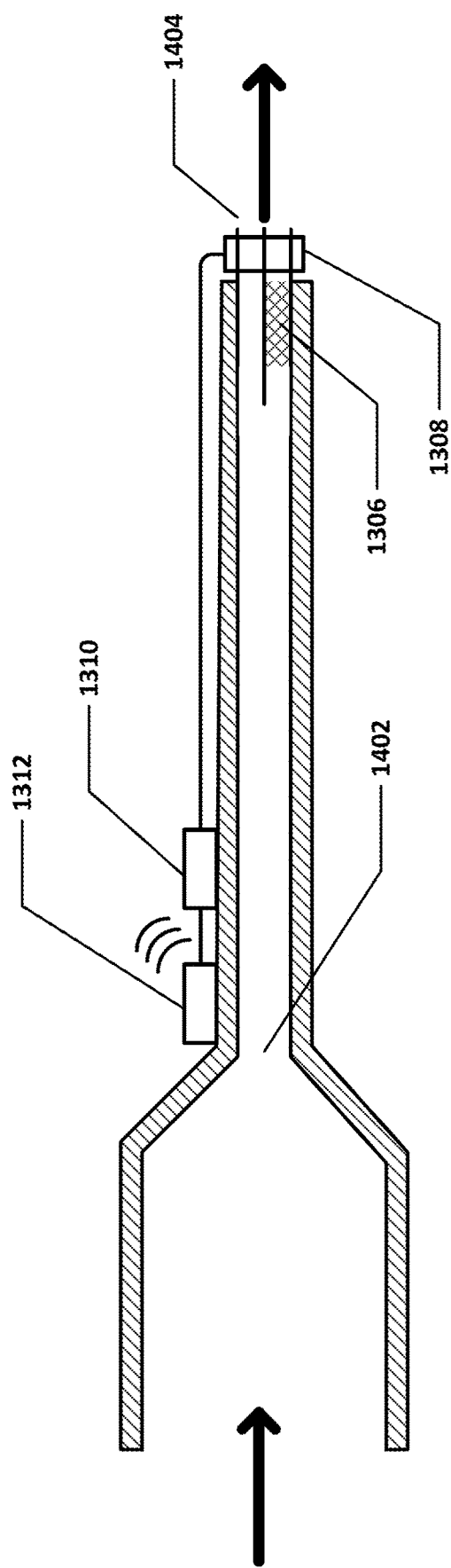
FIG. 14 shows an embodiment in which the restrictor and the sampling exit are combined

FIG. 14 shows an embodiment in which the restrictor and the sampling exit are combined. Restrictor 1402 reduces the turbulence in the airflow as air is breathed in and out of the airway device. Breathed air exits and may enter via outlet 1404. Differential pressure sensor 1308 may allow air to flow through it or alongside it to exit the airway device, or alternatively, the airway device may have an additional air exit (not shown). Note that this figure is showing an exhalation lumen only. A separate inhalation lumen may be incorporated into the device and/or the subject may be asked to inhale separately, either through his/her nose, or by removing the device from his/her mouth.

Note that the restrictor could be anything suitable, such as a flow control valve, a pressure control valve, etc.

Figure 15:
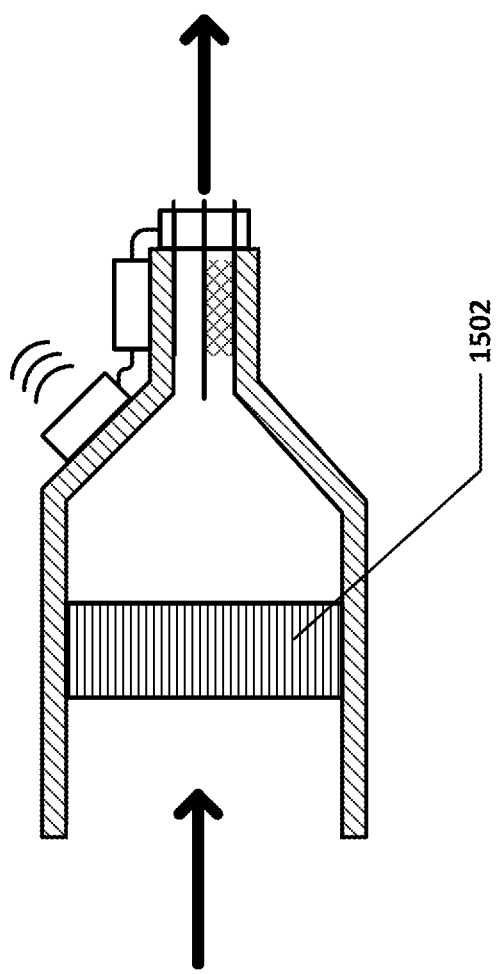
FIG. 15 shows an embodiment which incorporates a flow filter.

FIG. 15 shows an embodiment which incorporates a flow filter. Flow filter 1502 decreases the turbulence of the airflow coming into the airway device. In this embodiment, flow filter 1502 is used instead of a restrictor. The airway device may have an additional air exit (not shown). Flow filter 1502 may be made out of any suitable material such as polymer and in any suitable configuration such as a honeycomb or parallel capillary configuration. Note that this figure is showing an exhalation lumen only. A separate inhalation lumen may be incorporated into the device and/or the subject may be asked to inhale separately, either through his/her nose, or by removing the device from his/her mouth.

Any of the embodiments herein can be adapted to be used inside the mouth, or partially inside the mouth. For example, an airway device deeper inside the mouth may be advantageous in keeping the airway open for cleaner pressure measurements. Furthermore, any of the embodiments herein may also be adapted to be used with patients who are tracheally intubated, in which case the devices described are attached to or in-line with the tracheal tube.

Figure 16:
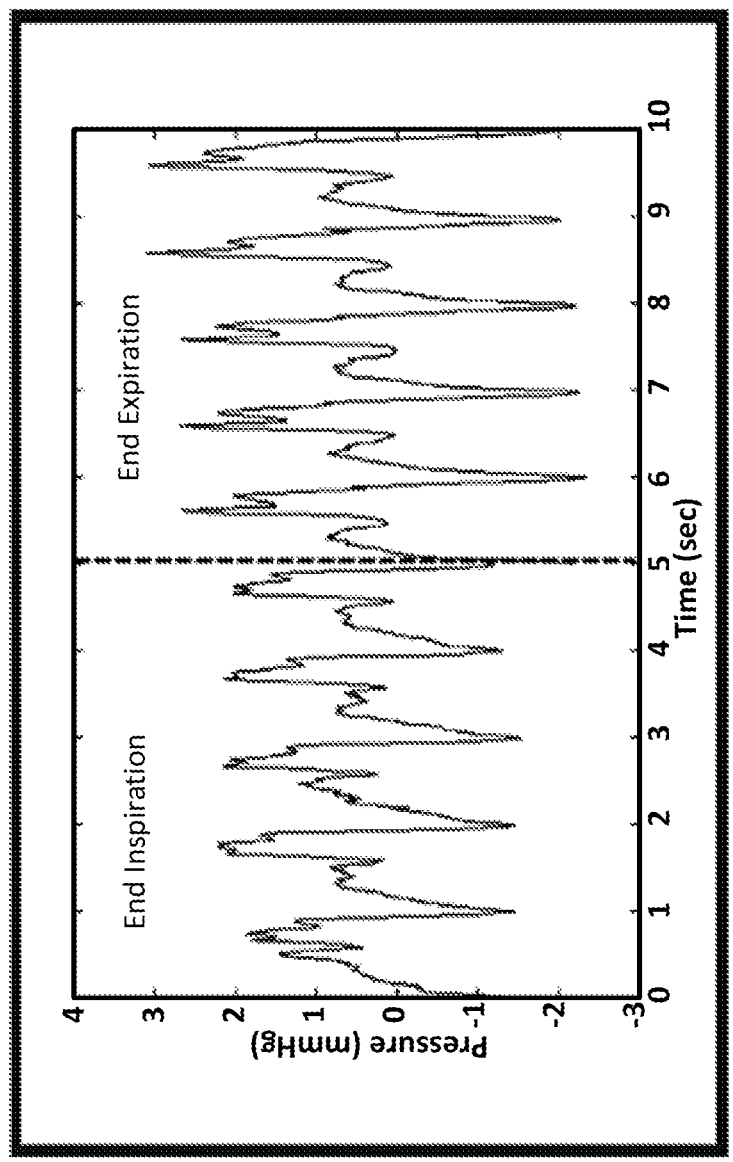
FIG. 16 shows a graph which demonstrates pulse pressure variability.

FIG. 16 shows a graph which demonstrates pulse pressure variability. As mentioned earlier, variability in the respiratory pulse pressure waveform can be used to determine hydration status, as well as volume status, and also pulmonary artery compliance. The graph in FIG. 16 shows the pulse pressure at end inspiration and at end expiration. Pulse pressure is defined as the difference between the systolic and diastolic pressure readings, or the amplitude of the waveform (lowest point to highest point). The difference in amplitude between these two waveforms is the pulse pressure variability. A large variability may indicate dehydration, where a decrease in variability over time may be an indicator that hydration is being restored or has been restored.

Figure 17:
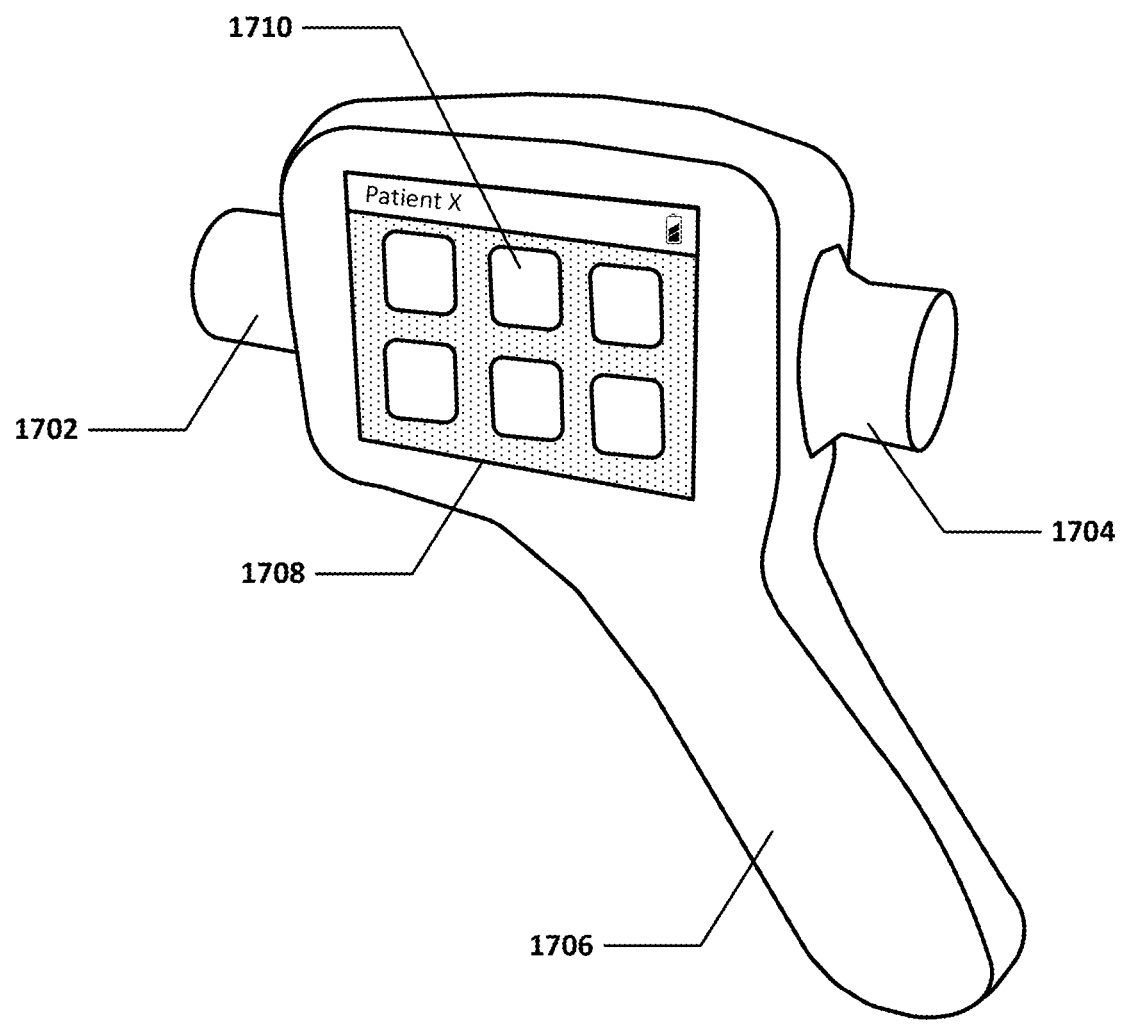
FIG. 17 shows an embodiment of the airway device/controller which includes a hand piece and at least some of the controller functions.

FIG. 17 shows an embodiment of the airway device/controller which includes a hand piece and at least some of the controller functions. The airway device of this embodiment includes 2 mouthpieces 1702 and 1704. The user breaths into one of these mouthpieces and breath exits through the other mouthpiece. Hand piece 1706 is held by the user or by the user's physician. Display 1708 displays one or more display areas 1710. These display areas may include buttons, or links, to more information, such as settings, waveforms, including waveforms showing HR (heart rate), SV (stroke volume), CO (cardiac output), PAC (pulmonary arterial compliance, etc., analytical results of waveform analysis, triggers for alarms/notices, etc. The airway device/controller of this embodiment may communicate wirelessly, or in a wired manner with one or more mobile devices, computers, servers, etc.

Figure 18:
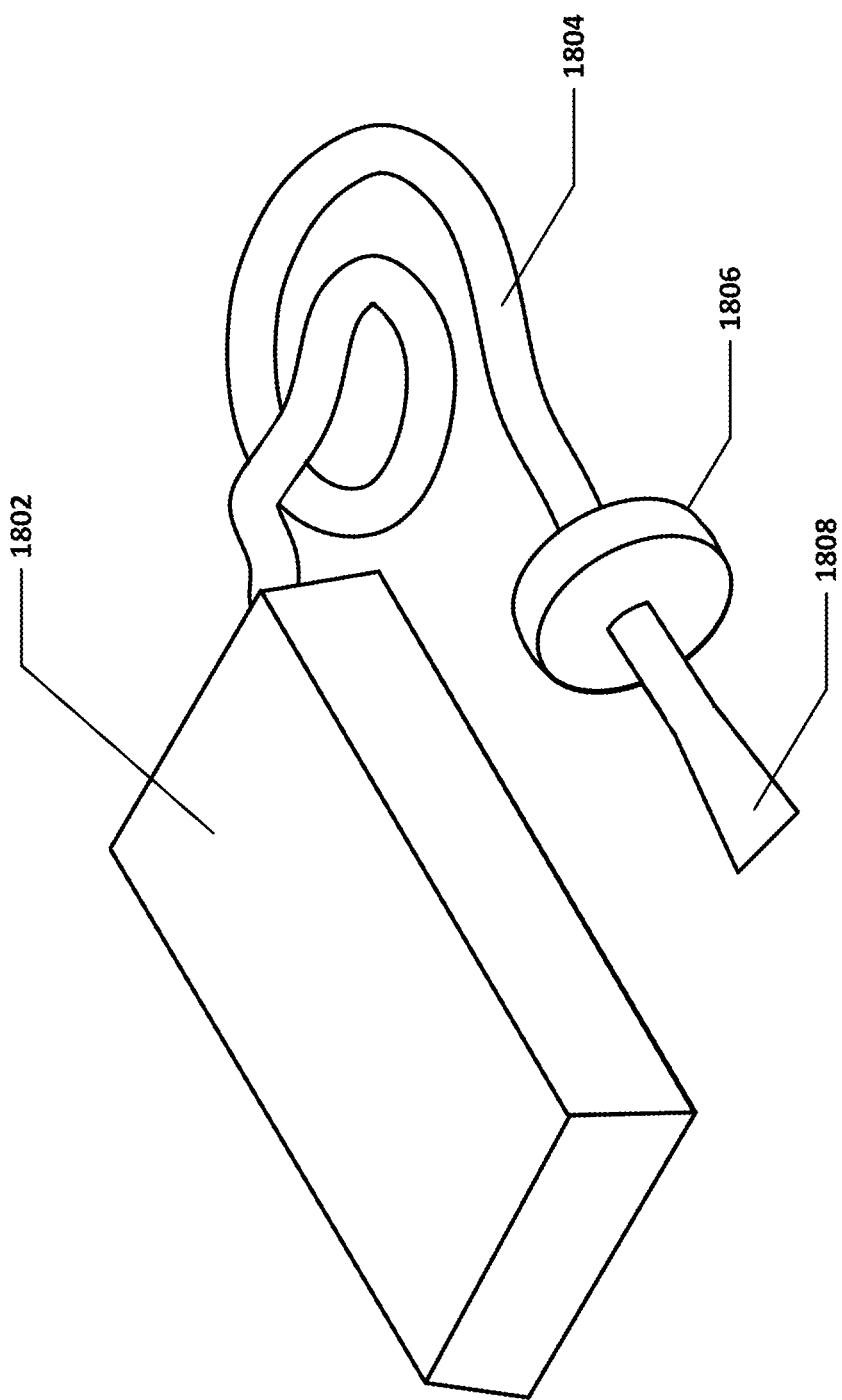
FIG. 18 shows another embodiment of the airway device/controller.

FIG. 18 shows another embodiment of the airway device/controller. This embodiment includes controller 1802, signal transmission tubing 1804, heat-moisture exchanger/filter 1806 and mouthpiece 1808. In this embodiment, the pressure/flow sensor may be in the controller. In use, during user breathing into the mouthpiece, the pressure in the airway is transmitted to the pressure/flow sensor via mouthpiece 1808 and tubing 1804. Note that controller 1802 may be in communication with a computer/mobile device/networked server etc., which may include some of the controller functions.

Embodiments of the airway device/controller may also be incorporated with a standard or specialized inhaler, for example for asthma. The airway device/controller in these embodiments may include a feature which tracks usage of the airway device and/or inhaler to monitor use compliance.

Embodiments of the airway device/controller may include integration with electronic health records (EMR) or electronic health records or other systems. For example, data from the controller may be transmitted wirelessly (or wired) to a server in the internet which integrates the data with that of an EMR. The patient ID (possibly anonymized) may be integrated into the metadata of the data transmitted by the controller so that the data can be integrated with the correct patient's medical record.

Data from multiple airway devices/controllers may be collected and aggregated and analyzed for trends. This data may be anonymized to comply with privacy rules.

In some embodiments of the airway device/controller, respiratory sinus arrhythmias (changes in heart rate due to breathing) may be tracked as an indicator of heart health or heart failure. Deviations from trends may be indicative of heart failure issues and may provide an alert. Because the data collected by the airway device may be continuous, for example, while the user sleeps, deviations from the norm (either for that patient or for a patient population) may indicate changes in health, and in particular, heart health.

In some embodiments of the airway device/controller, the device is used in an ambulatory manner. In other words, the user may use the device while walking around, watching TV, working, sleeping, resting, exercising or while performing everyday activities. The user is not tied to a stationary device, hospital nor clinic.

Sensors connected to the airway device/controller may include a blood oxygen saturation sensor or a blood CO2 saturation sensor or any other type of oxygen/CO2 sensor. For example, blood oxygen saturation may be determined by a pulse oximetry sensor in contact with the lips, tongue, oral mucosa and/or finger/extremities. This signal and/or an EKG signal collected from one or more EKG sensors (which may be in contact with these, or other, locations) may be used to determine pulse transit time.

Tissue O2/CO2 may be determined using an air tonometry sensor in contact with, or in proximity to, the tongue or oral mucosa or elsewhere. This type of sensor may include an air permeable membrane between the sensor and the body.

Absolute stroke volume may also be determined as follows. The volume or air displaced by each cardiac contraction due to pressure changes is determined by first determining the volume of air in the lungs. This may be done in one or more of several ways:

1) pulsed air method—A known volume of air is pulsed into the lungs and the change in pressure is measured. From this, the volume of dead space in the lungs may be determined.

2) spirometry—Total lung volume can be estimated from spirometry.

3) gas dilution—A known quantity and concentration of a target gas is infused into the lungs. The concentration of the target gas is then measured in the exhaled air exhaled to determine how much air has mixed with the target gas, thus providing an estimate of lung volume.

Stroke volume variability may also be determined/calculated. For example, the controller may prompt the user to breathe in deeply. The controller may use data captured from a sensor/sensors to determine stroke volume measurements at end inhalation and at end expiration-potentially to determine stroke volume variability. The controller may correct for changes in cardiac pulse size due to change in lung volume using spirometry (which measures breath volume) or the pulsed air method, or gas dilution techniques.

Spirometry may be used to measure one or more of several parameters, including: Vital capacity (VC), Forced vital capacity (FVC), Forced expiratory volume (FEV) at timed intervals of 0.5, 1.0 (FEV1), 2.0, 3.0 seconds, and other intervals, forced expiratory flow 25-75% (FEF 25-75), maximal voluntary ventilation (MVV), also known as Maximum breathing capacity, Peak Expiratory Flow (PEF), and any other parameters. Other tests may be performed. Results may be provided in raw data (liters, liters per second) and percent predicted—the test result as a percent of the "predicted values" for the patients of similar characteristics (height, age, sex, and sometimes race and weight), or the results may be provided in other ways.

In some embodiments of the airway device/controller, an ECG signal of the user is collected simultaneously to the cardiogenic oscillation data. In this way, the precise length and/or timing of a heartbeat can be determined (by the ECG signal) and the cardiogenic oscillation pressure curve can be divided up into precise heartbeats. In other words, one or more cardiogenic oscillation curves, each relating to one heartbeat, can be collected and identified and averaged, because the start and end of the cardiogenic oscillation curve relating to each heartbeat is precisely identified by the ECG signal. This allows collecting more than one cardiogenic oscillation curve and averaging them to get more accurate cardiogenic oscillation curve data. One or more ECG sensor/electrode(s) may be placed on the mouthpiece, or handheld portion of the airway device. ECG sensor/electrode(s) may be in contact with the user's mouth, finger(s), hand(s), or elsewhere on the body. Various features of the ECG curve may be used to "gate" the cardiogenic oscillation pressure curve. For example, the R peak, or alternatively the P, Q, S, T, U areas may be used.

Alternatively, or in addition, the signal from a pulse oximeter/photoplethysmograph may be used to gate the cardiogenic oscillation pressure curve in the same way—to determine the precise length/timing of the heartbeat. The same way a feature of the ECG curve can be used as a gating feature (for example, using the time between subsequent peaks of the R-wave), a feature, peak, valley, slope, length etc. of the pulse oximeter curve may be used instead of, or in addition to, the ECG curve. Multiple ECG and/or multiple pulse oximeter signals may alternatively be used. For example, the device may have electrodes/sensors for pulse oximeter and ECG for each hand, resulting in 2 ECG signals in addition to 2 pulse oximeter signals. This allows the best signal to be used to gate the cardiogenic oscillation pressure curve. The best signal may be chosen by amplitude, identifiable peak, consistency, etc. In this way, a good signal is likely to be obtained even if the user is not touching, or in contact with, all of the electrodes/sensors perfectly. Where redundant sensors are used to gate the cardiogenic oscillation pressure curve, the redundant sensors may be set with different gains on each. In this way, if one of the signals maxes out, or rails, where the peak of the curve is difficult to identify, another signal may be lower and have more identifiable peaks. This situation may occur if a user is pressing the sensors with a lot of pressure. In this way, one device with different sensors set with differing gains, may accommodate users with different finger pressures.

Outliers, or less useful data, may also be removed using ECG and/or pulse oximetry signals from the analysis to optimize the analysis results. More than one collected ECG/pulse oximetry signal may also be used in the analysis. One or more pulse oximeter/photoplethysmograph sensor/electrode(s) may be placed on the mouthpiece, or handheld portion of the airway device. Pulse oximeter/photoplethysmograph sensor/electrode(s) may be in contact with the user's mouth, finger(s), hand(s), or elsewhere on the body.

Alternatively, or in addition, the signal from the rough pressure sensor may be used to gate the cardiogenic pressure curve in the same way—to determine the precise length/timing of the heartbeat. Any sensor that determines and communicates the length/timing of a heartbeat to the controller may be used to gate the cardiogenic oscillation pressure curve.

In any of the gating curves, a regularly repeating feature, or peak, of the curve may be used to assess the quality or relative quality of the gating curve to be used as gating, as well as for the gating itself.

Figure 19:
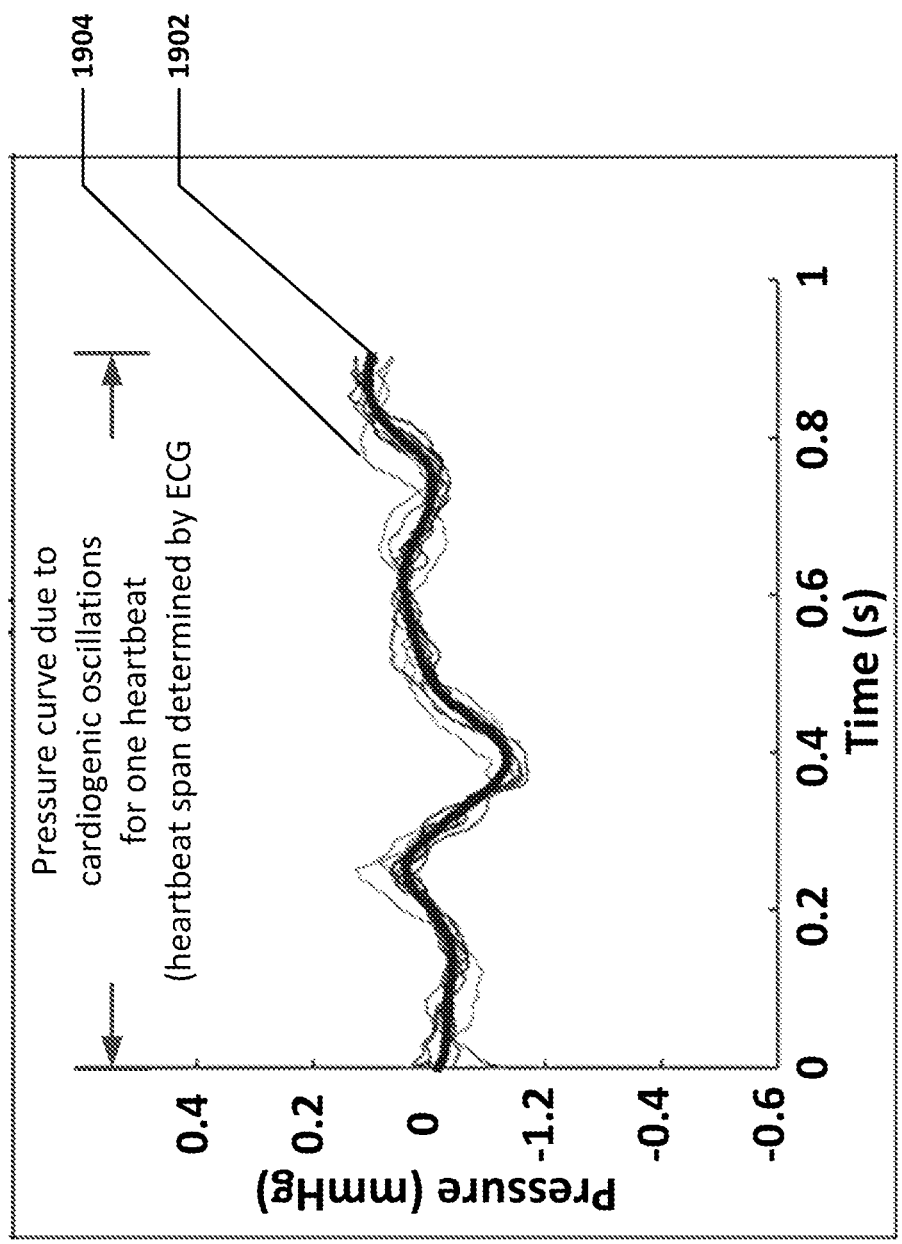
FIG. 19 shows several cardiogenic oscillation pressure curves and their average.

FIG. 19 shows several gated cardiogenic oscillation pressure curves layered on top of one another, along with the average of the curves. The thinner lines 1902 represent the individual cardiogenic oscillation curves obtained from several heartbeats. The heartbeats are separated on layered on top of each other and the average curve 1904 is calculated by the controller. The beginning and end point for each heartbeat can vary slightly over time making it difficult to average the curves without a way of precisely identifying the start and end point of each heartbeat (i.e., gating). Here, the controller does this by using the simultaneously obtained ECG signal from the patient. By picking one or more points in the ECG, for example, the R peak, the beginning and end of each heartbeat can be precisely identified and as a result, cardiogenic oscillation curves from multiple heartbeats can be averaged. The controller may also be equipped to determine the best point in the ECG to use for the heartbeat identification, for example the ECG curve may be analyzed for the most consistent area/peak, the most identifiable area/peak, the sharpest peak/area etc.

In the analysis shown in FIG. 19, the median curve may be used instead of, or in combination with, the mean curve. To construct the median curve, the median value at each point in time (for example, at 1, 2, 3, . . . ms after detection of the R peak) is calculated. This may help to reduce the influence of individual outlier curves, although other techniques may be used to accomplish the same goal, such as excluding the points that fall outside a specified window of deviation when calculating the mean.

Analysis of the shape of the cardiogenic oscillation curve may provide information on the patient. It is also patient specific, meaning that even among healthy patients, the cardiogenic oscillation curve shape is unique to each individual. In this way, the shape of the curve can be used as a signature to identify a patient. Changes in the cardiogenic oscillation curve may indicate specific disease states, or relative disease states. For example, the shape of the curve (or the change in the shape of the curve compared to normal or over time) may be analyzed to determine, and/or track over time, any of the following disease states.

Aortic stenosis
Aortic insufficiency
Mitral stenosis
Mitral insufficiency (regurgitation)
Pulmonary stenosis
Tricuspid stenosis
Tricuspid regurgitation
Pulmonary hypertension
Pulmonary fibrosis
congestive heart failure
Acute respiratory distress syndrome
Ventilator-acquired pneumonia
Pneumonia
Atrial Septal Defect
Patent Foramen Ovale
Single ventricle
Others In addition, changes to the shape of the cardiogenic oscillation curve over time, or with the patient in different positions, may indicate other patient parameters such as hydration. For example, a cardiogenic oscillation curve which appears to show improvement in PAC when the patient's legs are raised may be an indicator of dehydration. Hydration status may also be evaluated by changing the patient's position and/or breathing pressure. For example, the user may be prompted by the controller to take a measurement while standing, supine, sitting, legs raised, at a specific angle, inverted, etc. The relationship between or among these readings may be used in the data analysis to determine patient health. For example, the ratio between supine COS data and sitting COS data may be used in the analysis.

In some embodiments, any cardiovascular and/or pulmonary parameter may be collected in more than one patient position and the relationship between the parameters used to determine the health of the patient. For example, other available devices, such as the CardioMEMS™ device, manufactured by St. Jude Medical, may be used to collect a patient parameter, such as pulmonary artery pressure, when the patient is in more than one position. The data collected at these different positions can be used in conjunction with each another (for example, a ratio of data sitting and supine) to determine patient health.

In some embodiments of the airway device/controller, the user is prompted to breathe in one or more specific ways to obtain the pressure signal. The user may be asked to breathe (exhale, inhale or both or neither or MVM) into the device while simultaneously the controller controls a display which displays feedback on the pressure, the time, or other parameter, of the user's breathing. For example, the user may be asked to exhale at a steady pressure, within a pressure range, for a certain duration of time, and the display may show the user feedback on that pressure, and time, such as lights, a graphic display, or alternatively, the controller may provide audible feedback.

Figure 20B:
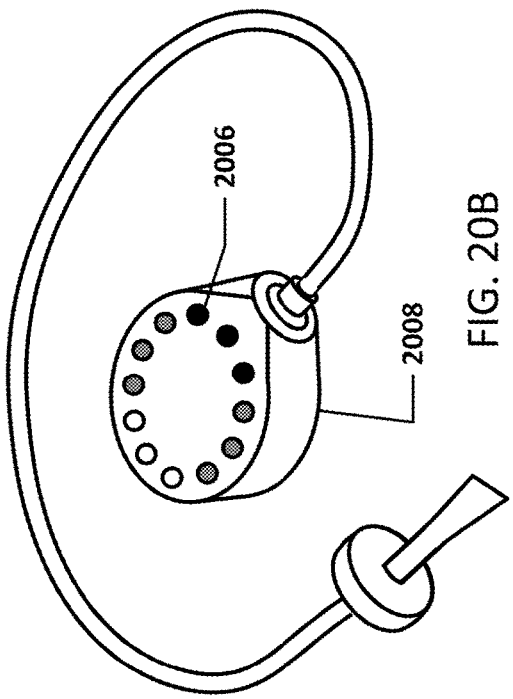
FIGS. 20A-C shows some alternative graphical displays.
Figure 20A:
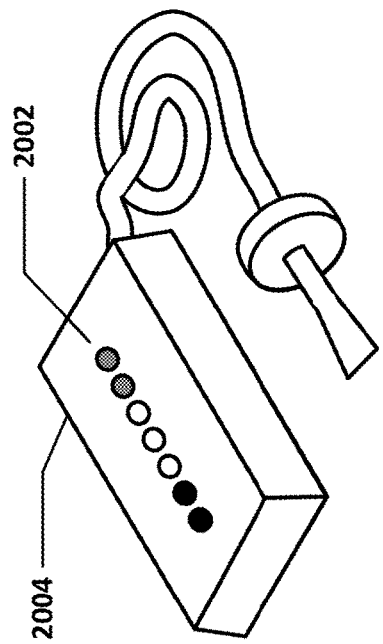
Figure 20C:
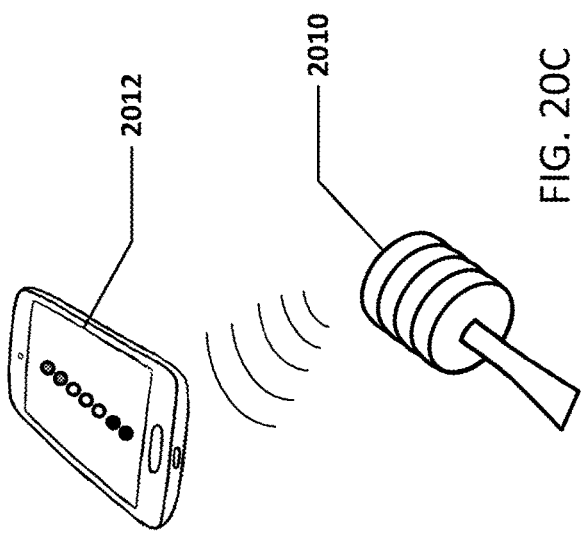

FIGS. 20A-C shows some alternative graphical displays which can guide the user to breathe at a constant pressure within a pressure range. FIG. 20A shows controller 2004 with indicator lights 2002. In this example, there are three ranges of lights with different colors, brightness, shape, etc. The lights indicate when the exhale pressure is too high, too low, or in range. In this example, the middle 3 lights show that the exhale pressure is in the optimal range. The user exhales into the mouthpiece and tries to hold his/her exhale pressure within the middle lights. Alternatives to lights may be used, including a graphical image, sounds, a dial, etc.

The graphical (or audible) display may also show the user when he/she is at the lower or higher end of the goal range (such as the pressure range), so that the user can make small adjustments to keep within range.

In some embodiments the goal exhale pressure is about 7 to about 8 mmHg. In some embodiments the goal exhale pressure is from about 9 to about 11 mmHg. In some embodiments the goal exhale pressure is from about 5 to about 7 mmHg. In some embodiments the goal exhale pressure is from about 5 to about 20 mmHg. In some embodiments the goal exhale pressure is from about 5 to about 15 mmHg. In some embodiments the goal exhale pressure is from about 10 to about 20 mmHg. In some embodiments the goal exhale pressure is from about 5 to about 10 mmHg. In some embodiments the goal exhale pressure is from about 7.5 to about 12.5 mmHg.

In some embodiments the goal exhale time is about 5 seconds. In some embodiments the goal exhale time is about 4-6 seconds. In some embodiments the goal exhale time is about 3-7 seconds. In some embodiments the goal exhale time is about 2-5 seconds. In some embodiments, the goal exhale time is set anywhere up to 10 seconds.

FIG. 20B shows an alternative arrangement of the graphical display. In this case, lights 2006 are used, but they are in a circular or oval pattern on a more curved controller 2008.

FIG. 20C shows an alternative arrangement of the airway device/controller. In this example, mouthpiece 2010 may include sensors, filters etc., and a wireless transmitter, such as a Bluetooth transmitter. The mouthpiece may contain components of the controller as well. At least some components of the controller are included in portable device 2012. The portable device may be a mobile phone, table, computer etc., and includes a wireless receiver and a display. In this embodiment, pressure sensor information is transmitted wirelessly to the controller device which displays or communicates feedback to the user. The feedback may include breathing pressure feedback, time, as well as any other feedback. The connection between the mouthpiece and the controller may be wired as well. Different components of the controller may be distributed between the mouthpiece and the controller.

Some components of the controller may also exist remotely, for example on an internet connected server, which is in communication with the local controller.

FIGS. 21A-B show embodiments of the airway device/controller which include a "sensor hand-piece". A sensor hand-piece includes sensors and/or electrodes on the hand-piece itself for sensing various physiological parameters. The sensors/electrodes may be on the surface of the sensor hand-piece where they are easily in contact with one or more fingers and/or hands of the user. The sensor hand-piece may include sensors such as ECG sensors/electrodes, and/or pulse oximeter/photoplethysmograph sensors/electrodes on its surface. In this embodiment the sensor hand-piece is an ergonomic case which the user holds so that his/her fingers are in contact with various and appropriate sensors which are on the surface of the case. In FIG. 21A sensor hand-piece 2102 includes ECG sensors/electrodes 2104 and pulse oximeter/photoplethysmograph sensor/electrode 2106. The user may hold the sensor hand-piece with both hands so that 2 fingers/thumbs are touching the ECG sensors and another finger/thumb is touching the pulse oximeter sensor. Alternatively, the different types of sensors may be combined so that fewer fingers are required.

FIG. 21B shows a sensor hand-piece connected to a controller. This connection may be wireless or wired. Alternatively, the sensor hand-piece may be combined with the controller—the controller/sensor hand-piece may include a graphical display as well as sensors.

In some embodiments the airway device/controller is incorporated into a CPAP (Continuous Positive Airway Pressure) device. In these embodiments the controller may control the positive pressure delivered by the CPAP device based on the controller's analysis of the cardiogenic oscillation pressure curve.

Figure 22:
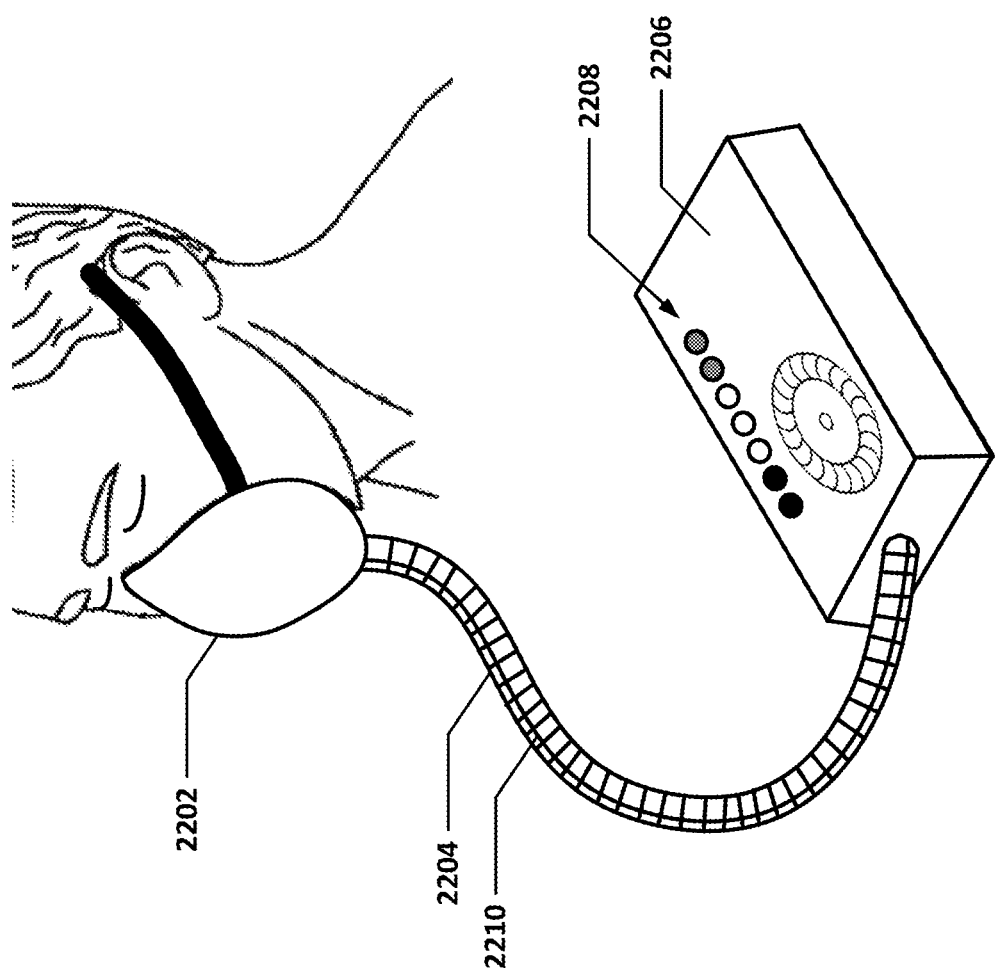
FIG. 22 shows an embodiment of the airway device/controller which has been incorporated into a CPAP device.

FIG. 22 shows an embodiment of the airway device/controller which has been incorporated into a CPAP device. The various sensors may exist in mask 2202, ventilation tubing 2204 or controller 2206. A handheld unit, such as the one shown in FIGS. 21A/B may also be present for use when the user is awake, and may or may not include sensors such as ECG and photoplethysmograph sensors. Indicator graphics 2208 may also be present for setup, or for when the user is awake. Sensors in the mask may communicate with the controller via wire 2210 embedded in the ventilation tubing or the communication may be wireless. No communication may be necessary if the sensors are located in the controller rather than the mask. Cardiogenic oscillations and other parameters (such as ECG, pulse, etc.) may be sensed via the CPAP system via sensors in the mask, the controller, or elsewhere, such as in a sensor hand-piece. The CPAP device may be run in a test or setup mode, to obtain readings when the user is awake, and also in a sleeping mode, to obtain readings while the user is sleeping. For example, the user may be prompted to breathe at a certain pressure for a certain time frame while awake to set a baseline. Readings may then be collected while the user is sleeping and adjustments to the CPAP airway pressure may be automatically adjusted based on changes to the readings. In addition, or alternatively, an alert may sound to wake the user when certain changes in readings are detected.

In embodiments of the airway device which are combined with a CPAP device, or other positive pressure device, heart health may not only be diagnosed, but treated. Because the airway device measures the exact timing of heartbeats (via ECG, photoplethysmograph, rough breath pressure, cardiogenic oscillations, etc.), positive pressure can be applied through the airway to the lungs in synchrony with the heartbeat. Pulmonary pressure can be increased after ventricular contraction, and decreased before the next heart contraction, to offload the work of the heart.

Figure 23:
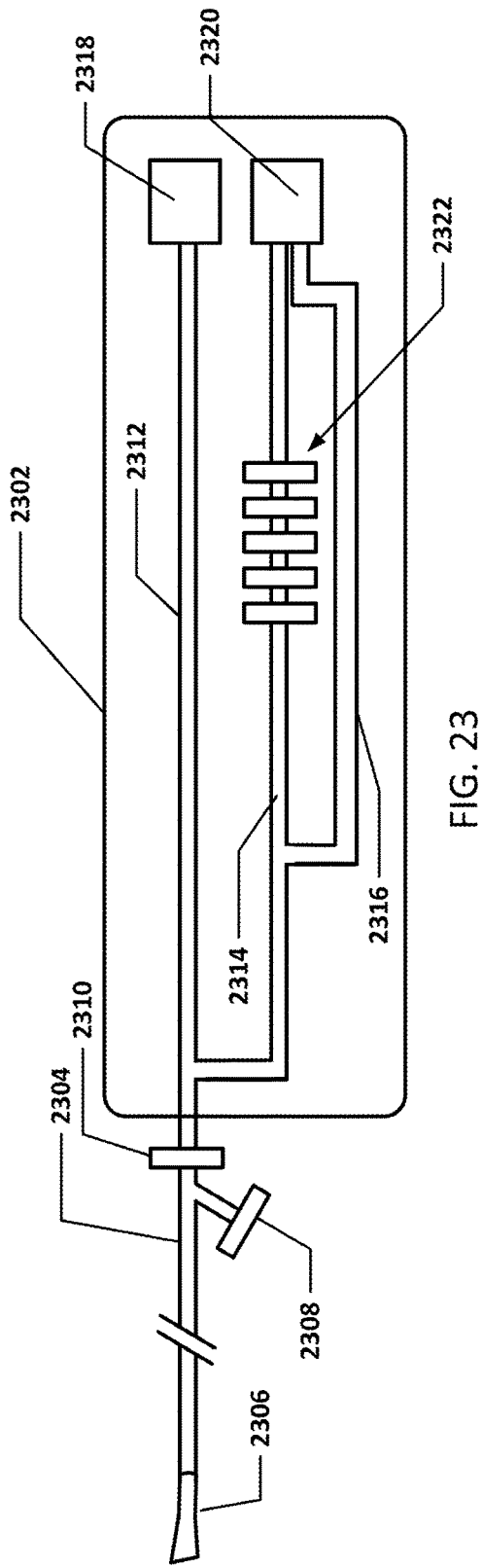
FIG. 23 shows an embodiment of the airway device/controller which may be standalone, or incorporated into a CPAP device.
Figure 24:
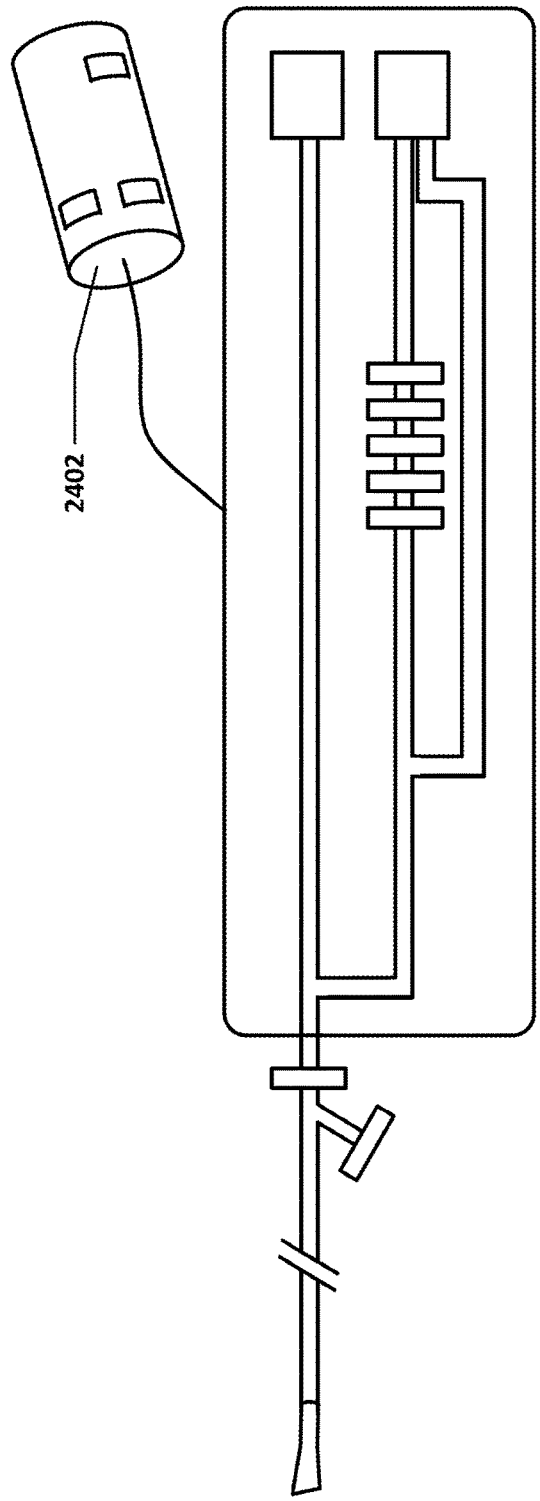
FIG. 24 shows an embodiment of the airway device/controller which may be standalone, or incorporated into a CPAP device.

FIG. 23 shows an embodiment of the airway device/controller which may be standalone, or incorporated into a CPAP device, or used with additional controller components. Case 2302 houses the mechanisms of the controller. Airway tubing 2304 is in fluid communication between the controller and mouthpiece 2306. In this embodiment, all of the sensors and the controller are within casing 2302, but other embodiments may exist with sensor and controller functions elsewhere, for example as shown in FIG. 24 where sensor hand-piece 2402, including ECG and pulse oximetry sensors, is shown, and/or in embodiments where some or all of the controller computational functions are performed on a remote server.

Figure 25:
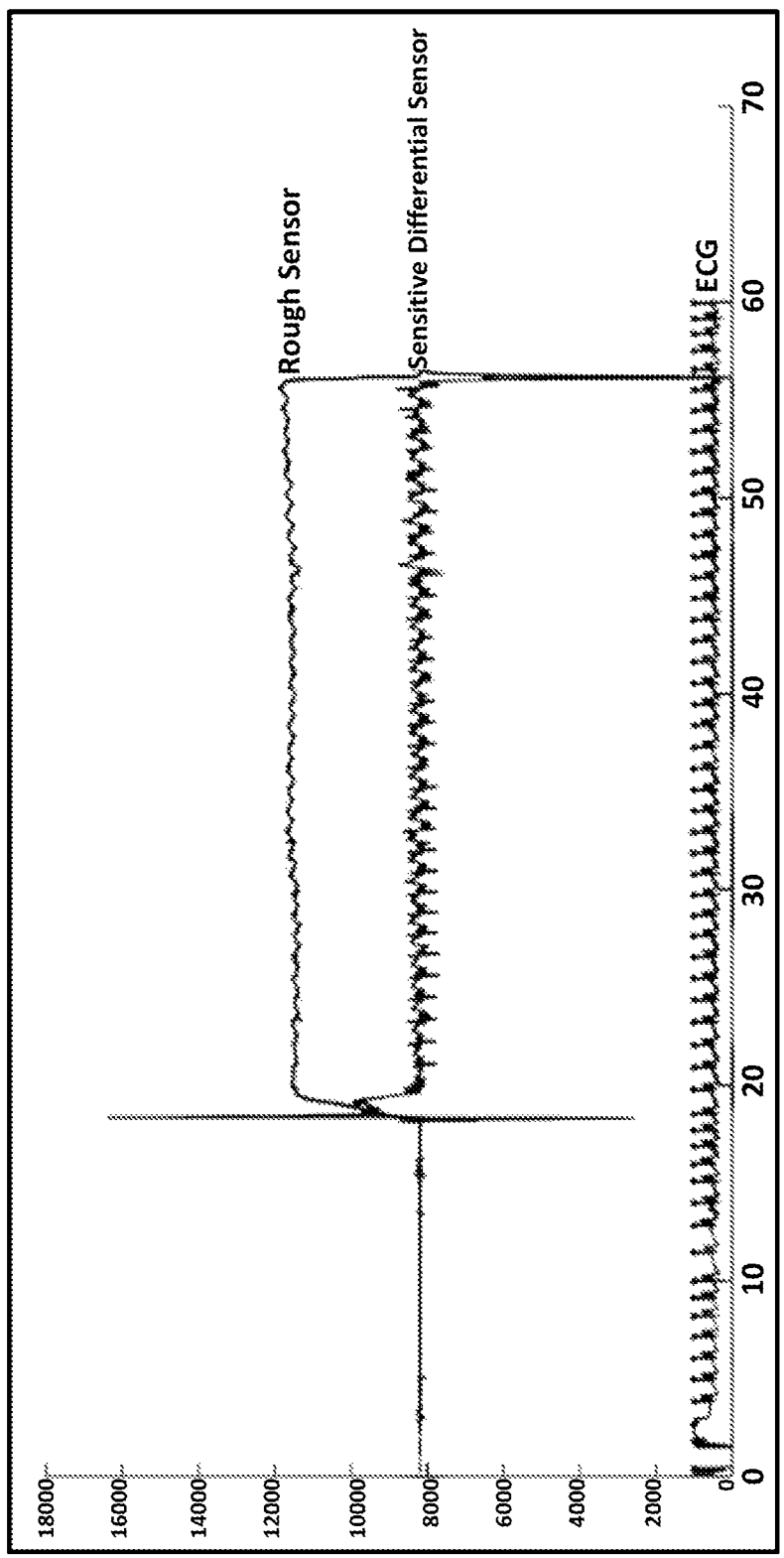
FIG. 25 shows a graph of the pressure signal from a rough pressure sensor, a sensitive differential pressure sensor and an ECG.

Mechanical filters 2308 and 2310 help restrict and control the flow of air through the airway tubing. Inside the case, rough pressure sensor tubing 2312 is in fluid communication with rough pressure sensor 2318 and airway tubing 2304. Fine differential pressure sensor 2320 is in fluid communication with tubings 2314 and 2316 which are in fluid communication with rough pressure sensor tubing 2312. Inline flow restrictor 2322 is incorporated into tubing 2314 to restrict flow through one tubing in fluid communication with fine differential pressure sensor 2320. The other tubing, tubing 2316, either does not have a flow restrictor, or has a flow restrictor with a different restriction level than flow restrictor 2322. Flow restrictor 2322 may comprise one or more mechanical filters. The signal from rough pressure sensor 2318 may be subtracted from the signal from fine differential pressure sensor 2320 to remove artifacts from breathing, moving, coughing, etc. See FIG. 25. Alternatively, the pressure signal from the rough sensor may be used to determine that the user is exhaling at a constant and targeted pressure. For example, the rough pressure sensor signal may drive the graphic display, such as the lights to show the user when he/she is in the target pressure range. In this situation, the cardiogenic oscillation signal would be extracted from the fine differential pressure sensor.

Fine pressure sensor sensitivity may be around +/−2 mmHg. Rough pressure sensor sensitivity may be around +/−10 mmHg. Alternatively, fine pressure sensor sensitivity may be around +/−0.5 mmHg-+/−3 mmHg. Rough pressure sensor sensitivity may be around +/−5 mmHg-+/−15 mmHg. Fine pressure sensor or rough pressure sensor may be differential pressure sensors.

As mentioned elsewhere herein, pulse transit time may be determined by evaluating the time between the ECG signal (for example, the R peak) and the heartbeat as measured by pulse oximetry/photoplethysmograph. Pulse transit time may also be determined by determining the time between ECG signal and a peak in the cardiogenic oscillation curve. This may provide different information including heart valve opening pressure and/or opening times.

FIGS. 26A and 26B show 2 embodiments of the mouthpiece area of the airway device. Mouthpiece 2602 with mouthpiece opening 2604 is in communication with filter segment 2608 which is in communication with airway tubing 2610 so that a lumen runs from mouthpiece opening 2604 to the controller (not shown). Filter segment 2608 contains a hydrophobic filter membrane with a pore size ranging from about 2 micron to about 4 micron. Alternatively, the pore size of the filter ranges from about 1 micron to about 5 micron. Preferably, the filter pore size prevents water vapor from passing through the filter.

This embodiment includes resistance control orifice 2606 which controls the resistance felt by the user while blowing through the mouthpiece. In some embodiments, the user is asked to exhale at a relative constant exhale pressure for about 1 to 5 or about 5 to 10 seconds. The resistance control orifice can control the exhale resistance. A smaller sized resistance control orifice will equate to a higher exhale resistance. A larger sized resistance control orifice, or multiple resistance orifices, will result in a lower exhale resistance. Preferably, the resistance control orifice is approximately circular in shape and ranges from about 0.3 mm to about 0.5 mm in diameter or longest dimension. Alternatively, the longest dimension of the resistance control orifice is from about 0.1 mm to about 1.0 mm. Alternatively, the longest dimension of the resistance control orifice is from about 0.5 mm to about 1.0 mm.

Filter segment 2608 may adapt to mouthpiece 2602 and/or airway tubing 2610 by a common luer type adapter or any other suitable adapter such as luer-lock, screw on, snap on, glue on adapter etc.

FIG. 26B shows an embodiment similar to that shown in FIG. 26A with the addition of orifice sheath 2612. The orifice sheath protects the resistance control orifice from blockage by the users finger or otherwise. The orifice sheath includes opening 2614 which allows air to freely flow out of (or into, during inhalation) the resistance control orifice even if the user has his/her fingers on the orifice/orifice sheath area. The orifice sheath is preferably made from a rigid material such as a polymer, and may be integral with mouthpiece 2602 and/or filter segment 2608.

Figure 27:
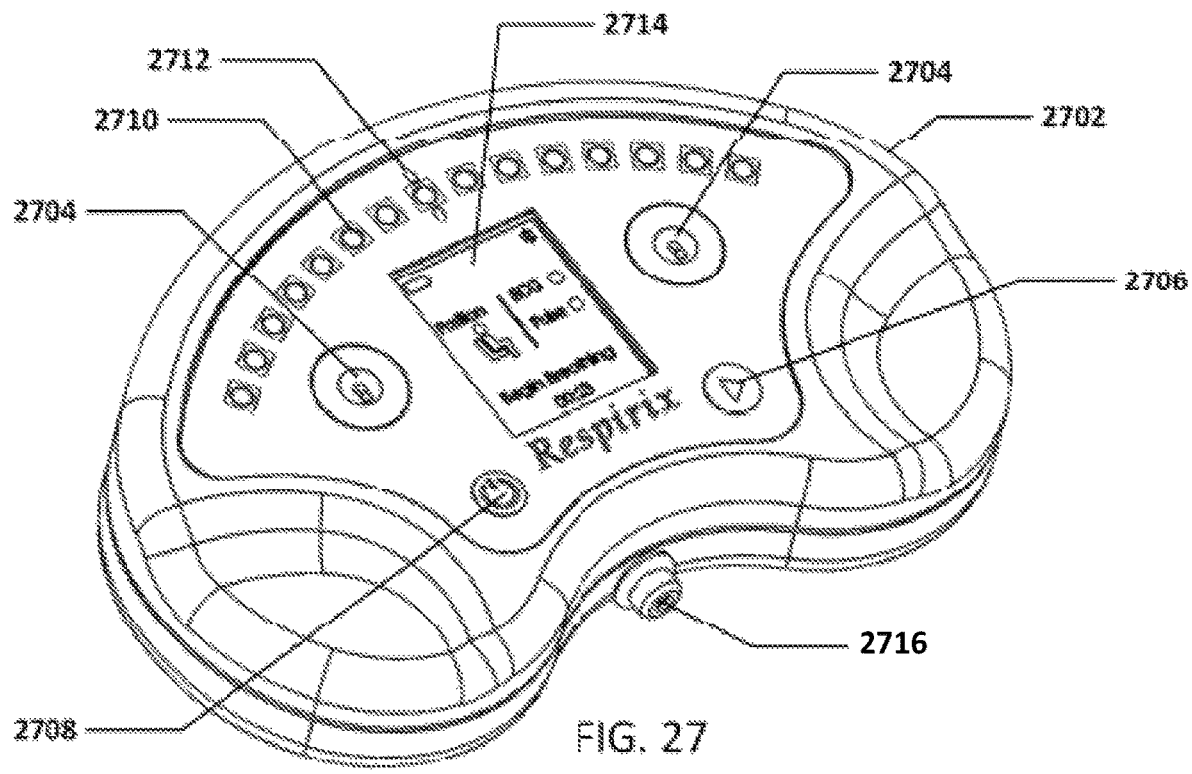
FIG. 27 shows a top view of an embodiment of the hand piece.
Figure 28:
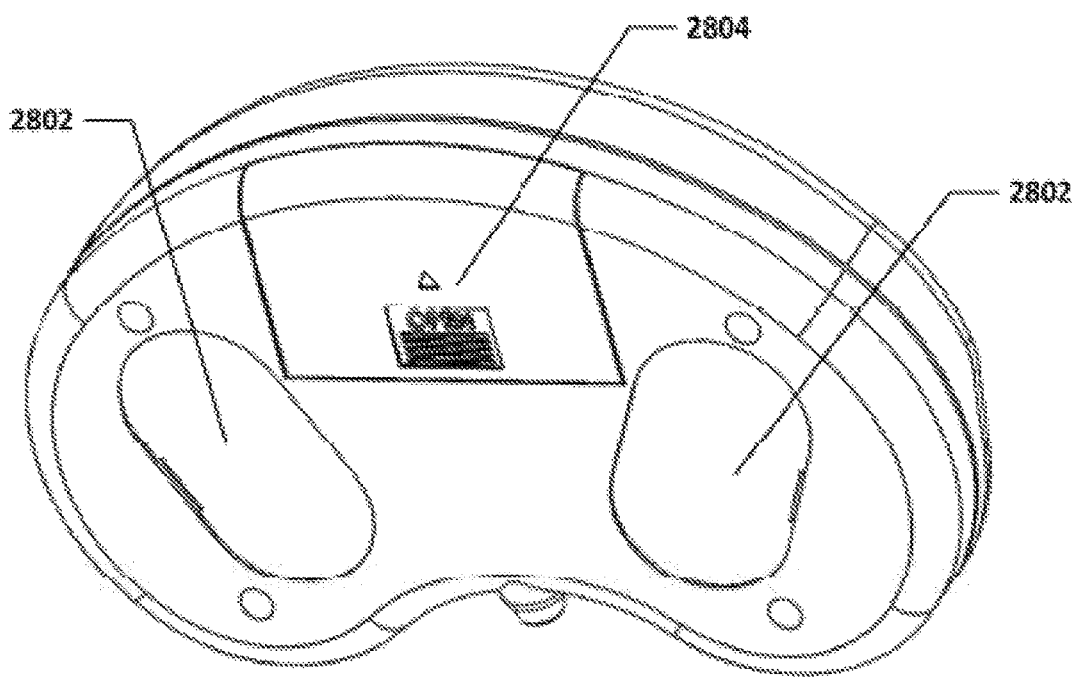
FIG. 28 shows a bottom view of an embodiment of the hand piece.

FIGS. 27 and 28 show the top view and bottom view, respectively, of an embodiment of a sensor hand piece of the airway device which includes at least some of the controller functions. The sensor hand piece includes casing 2702. On the casing top are one or more heart pulse sensors/electrodes (photoplethysmograph/pulse oximetry sensors) 2704, airway tubing connector 2706, power button 2708, breath pressure indicator or indicators 2710, breath pressure goal indicator or indicators 2712, display 2714, and mode button 2716.

FIG. 28 shows the bottom view of an embodiment of a sensor hand piece including ECG electrode or electrodes 2802 and battery cover 2804. Note that any of the sensors/electrodes may be anywhere on the case.

When holding the sensor hand piece, a user will preferably have one or both thumbs in contact with pulse sensor(s) 2704, and one or more fingers in contact with ECG electrode(s) 2802. Preferably, before the user places his/her fingers/thumbs on the sensors, he/she will place the mouthpiece in his/her mouth. However, if only one hand is necessary for the sensor contacts, the mouthpiece may be placed in the user's mouth at any time before testing begins.

During data collection, the user is guided through various steps either by display 2714, or audibly or both. Alternatively the display may be on the user's mobile phone/computer with other functions of the sensor hand piece in communication with the mobile phone/computer either by a wired connection, a wireless connection, or direct connection via a port in the mobile phone/computer. Indicator(s) 2710 may be lights, a visual bar, audible sounds, tactile feedback (such as vibration) etc. in this figure, the indicators are lights which indicate the exhale pressure as well as the consistency of the exhale pressure, and may also indicate when the exhale pressure has been consistently in the proper pressure range for the required time. Preferably, the user is guided by the indicators to hold a steady pressure. In addition or alternatively, the user is guided by the indicators to hold a particular target pressure. A target pressure may be preset or may be set depending on the individual user and the user's comfortable exhale pressure range for holding a steady exhale pressure. Pressure goal indicator 2712 may be fixed in place or may be movable to suit individual users. The software may also include the ability to adjust indicators 2710 so that goal indicator 2712 stays in the same location, but refers to different exhale pressures for different individuals. For example, as part of a set up procedure, the user may be asked to exhale at a comfortable pressure for x seconds. A button on the device may be pressed to set that pressure as the "goal" pressure for the particular individual.

Figure 29:
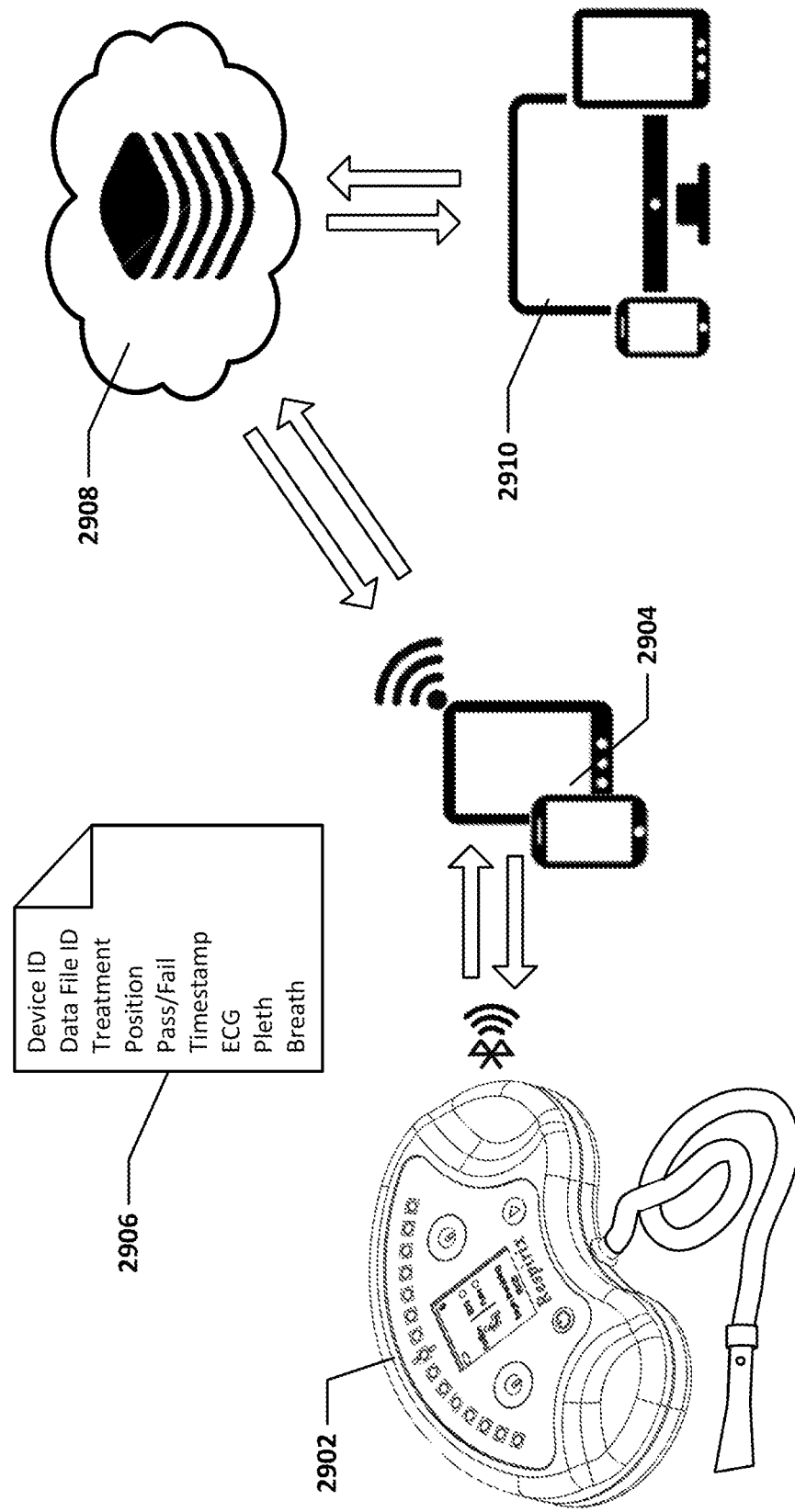
FIG. 29 shows how an embodiment of the airway device controller and how the system communicates data.

FIG. 29 shows how an embodiment of the airway device controller and the system communicates data. In this embodiment, the controller functions are distributed among sensor hand piece 2902, mobile phone/device/computer 2904, cloud/internet/intranet server 2908 and dashboard computer 2910. In general, data is collected via sensor hand piece 2902, communicated locally with mobile device 2904 (via Bluetooth, wifi, or other wired or wireless connection) which communicates remotely with server 2908 (via wifi, mobile network, wired or wireless communication etc.) which can then communicate with any device, such as a desktop computer, laptop computer, mobile device, tablet, client, etc. (via wifi, mobile network, wired or wireless communication etc.).

Data 2906 transferred from the sensor hand piece includes Device ID (the unique identifier of the hand piece, which may be in the form of a MAC address or other ID), Data File ID (the unique identifier of the data file within the device), Treatment data, Position data (sitting, lying down, etc.), Pass/Fail data (related to whether sensor data collected is adequate for analysis, may also be adequacy level data), Timestamp(s), ECG data, pulse oximeter/photoplethysmograph data, Breath data, and other relevant data.

Sensor hand piece 2902 may incorporate any of the embodiments disclosed herein. Server 2908 may be remote or local, and may be on the Internet, intranet or local network. Dashboard computer 2910 may have different access rights. For example, the patient/airway device user may have one access level, where a physician or an insurance company or a clinical trial administer or another type of administrator may have another access level. Data may be displayed in various ways depending on the user. For example, a clinical trial administrator may see data aggregated from more than one user, but may not see the identity of the users. The patient may see only his/her data and may see trends, alerts, suggestions etc. The patient's physician may see the data of several patients, each identified, with alerts, data trends, etc. The dashboard computer, or server, may be integrated with an electronic health record. Data from the airway device may be integrated with a patient's personal electronic health record. Data from the airway device may be used to make diagnoses either with or without data from other devices/sources. Server 2908 may include algorithms which incorporate and analyze data from the airway device and optionally other data collection devices to predict outcomes.

Figure 30:
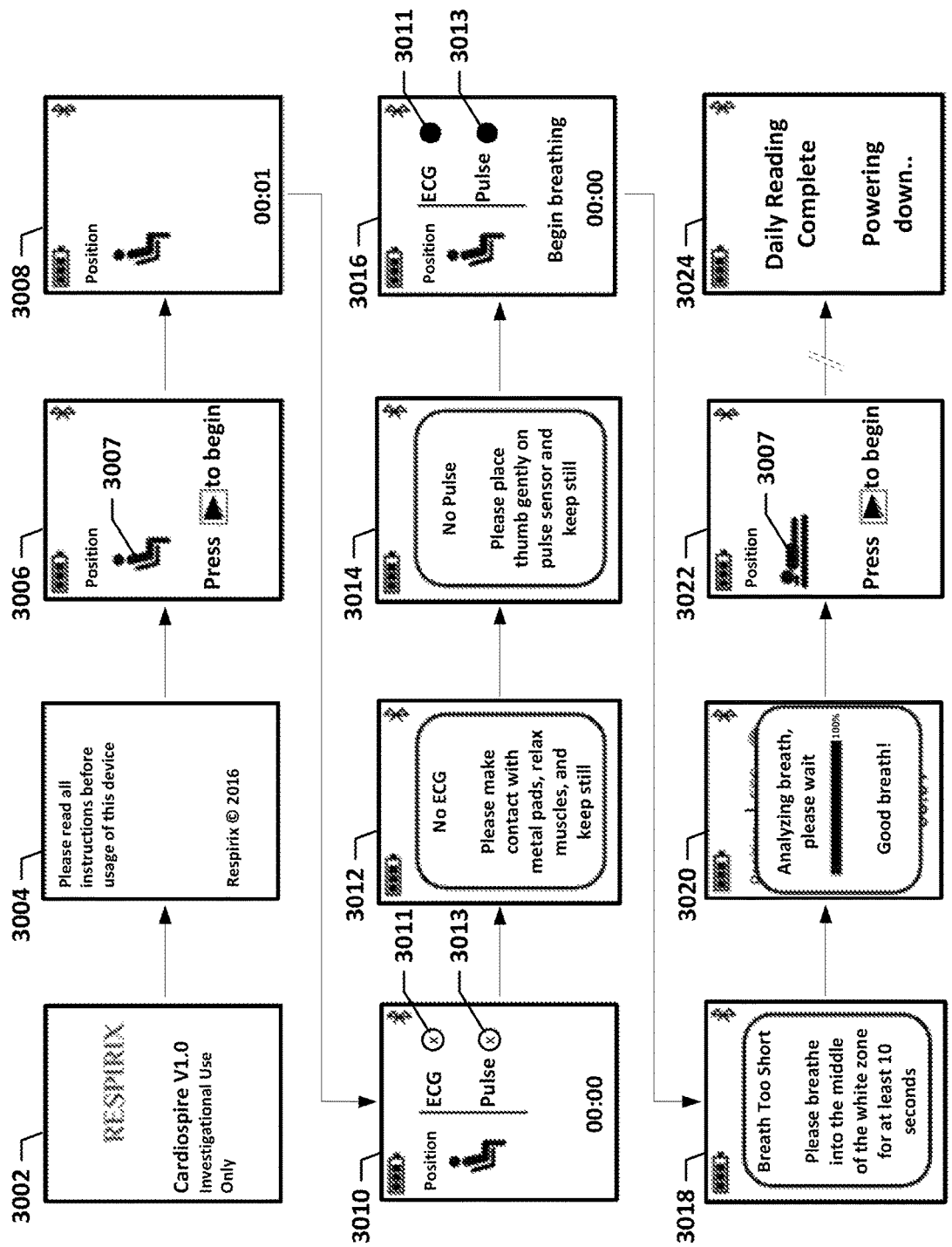
FIG. 30 shows examples of screens that may be shown on the display

FIG. 30 shows examples of screens that may be shown on display 2714 shown in FIG. 27. Screen 3002 shows a sample welcome screen. Screen 3004 shows a sample information screen. Screen 3006 shows a sample start screen, which includes positional indicator 3007 indicating in which position the user will start. For example here, the user will start in the sitting position. Other positions may include supine, supine with legs raised, standing, etc. A Bluetooth indicator shows that the user is connected to his/her mobile device via Bluetooth and the user is encouraged to push the mode button to begin the testing. The user may see more information including how to hold the hand piece and where to place his/her finger(s) and thumb(s). Screen 3008 shows that the testing has now begun. First the system will test to confirm that adequate contact with the sensors is sensed, by determining whether the ECG and pulse signals are adequate, as shown in screen 3010. "Adequate" or "good" may include measuring the signals over time to determine magnitude, consistency, shape, trends, or other attributes of the signals. ECG signal adequacy indicator 3011 and pulse signal adequacy indicator 3013 show an inadequate signal until an adequate signal is obtained. The indicators may show a red indicator, an open indicator, an X, or a sound or tactile indicator, such as a vibration which tells the user when the signal(s) is inadequate and/or adequate. Screen 3012 is a screen showing the user that the ECG signal is inadequate. This type of screen may pop up after multiple attempts at an adequate signal or when a signal has been inadequate for a certain period of time. Additional instruction may be provided to help the user obtain an adequate signal. Screen 3014 shows a similar screen when an adequate pulse signal has not been obtained.

Screen 3016 shows a screen that indicates that adequate ECG and pulse signals are being obtained. The user is then instructed to begin breathing. Breathing may mean natural breathing or a prolonged steady exhale or inhale. Preferably, the user is asked to produce a steady prolonged exhale. Again, the system evaluates the signal to determine if the breath signal is adequate or inadequate. The adequacy of a breath signal may include length of signal, consistency of signal, magnitude of signal, shape of signal (such as the pressure signal), existence of regular peaks, etc. Screen 3018 shows a sample screen which may be displayed if the breath signal is determined to be inadequate. The screen may provide additional information such as length of breath, steadiness of breath, magnitude of breath etc. For example, here the user is asked to breath for at least 10 seconds. The user is also asked to breath in the middle of the "white zone", meaning to breathe so that indicators 2710 shown in FIG. 27 are in the goal range. Keeping the indicator in the goal range will control both the amplitude of the breath signal as well as the steadiness of the breath signal. All of these prompts may be provided to the user or a different prompt may be provided depending on whether length, amplitude, or steadiness of the signal is lacking.

Screen 3020 shows the progress of the test when breath, ECG and pulse signals are all adequate. The system may analyze the results in real time to determine whether the total signal is adequate, meaning it can be analyzed properly. If the signal cannot be analyzed property, the user may be prompted to repeat the test.

Screen 3022 shows the beginning of the next test, which differs from the previous test by position. This screen, for example, shows that the user should now lie down. Once the user is lying down and presses the mode button, screens similar to those shown in screens 3008 through 3020 will be shown. Other factors in addition to position may be changed for different tests. For example, the user may be asked to exercise between tests, or breathe differently or for a different length of time. Screen 3024 is a sample end screen when all testing for the session is complete.

Figure 31:
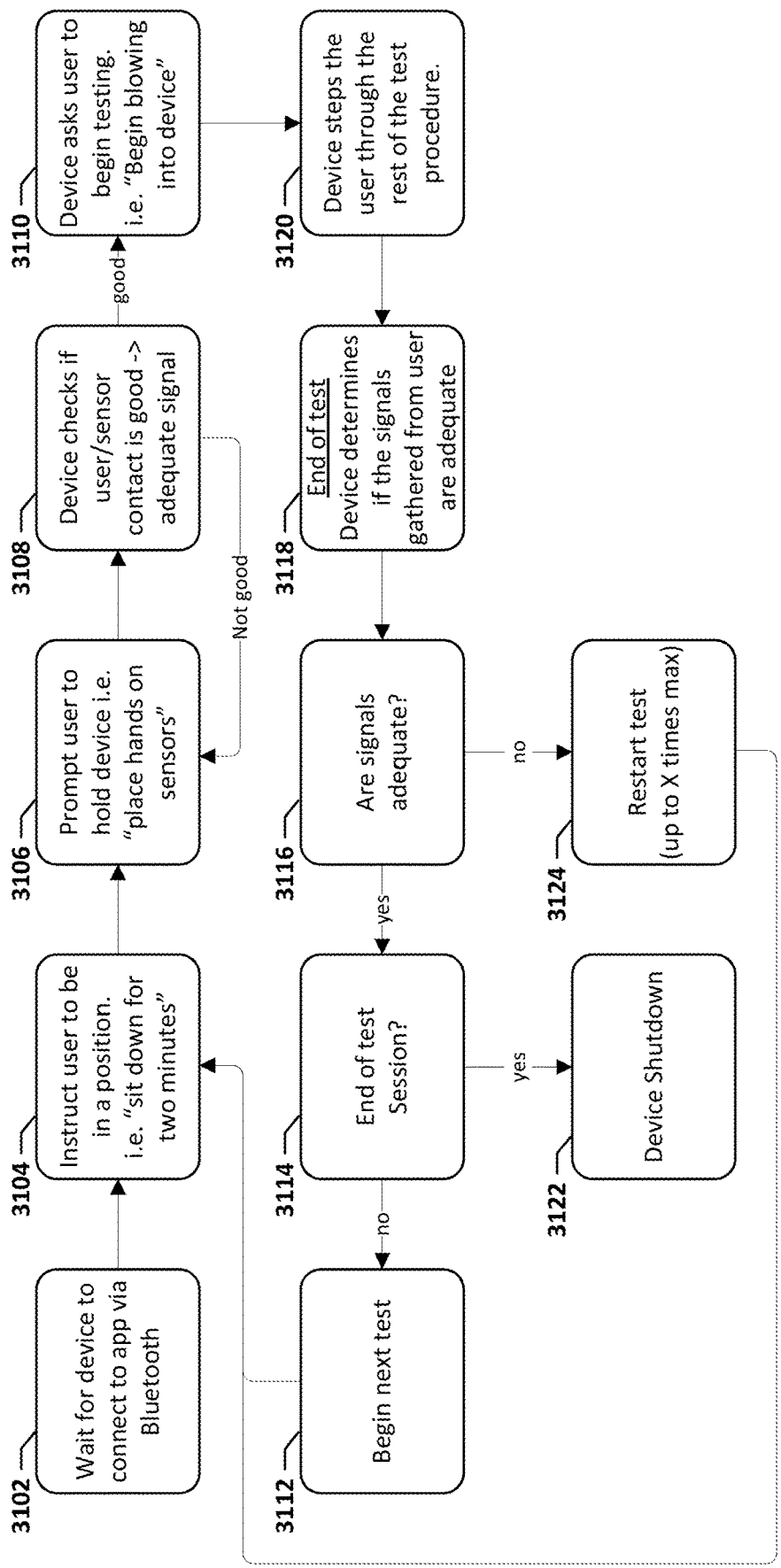
FIG. 31 outlines a method of use of an embodiment of the airway device/controller device.

FIG. 31 outlines a method of use of an embodiment of the airway device/controller device. These are steps that the controller performs in one embodiment. Step 3102 represents the controller in standby, waiting for a user to initiate the testing by connecting the hand piece to a mobile device via Bluetooth or other technology. Once the user has initiated the test, and connected via Bluetooth, the controller prompts the user to take a certain position, such as sitting, standing or lying down, as represented in step 3104. Step 3106 represents the controller prompting the user to put his/her finger(s) and thumb(s) on the appropriate sensors. More specific instructions may be given as well. Step 3108 represents the controller checking to see if the signals are adequate. If the signals are inadequate, the controller prompts the user in a way to increase the adequacy of the signal(s). If the signals are adequate, the controller moves onto step 3110 where the user is prompted to begin testing by blowing into the mouthpiece of the device. Screen 3112 represents the beginning of the next test. Step 3120 represents the controller gathering data from the hand piece sensors (i.e. ECG and pulse) as well as the breath sensor(s) (i.e. pressure and/or flow). Step 3118 represents the end of the test sequence. At this point, the controller determines whether the data collected during the test sequence are adequate—represented by step 3116. If the data are adequate, then the controller ends the current test session represented by step 3114. In step 3114, the controller prompts the user as to, or communicates to the user, whether there are any more tests that need to be performed, for example, in a different position. If there are more tests to be performed, the controller returns to step 3104. If there are no more tests to be performed, the controller shuts down the device as shown in step 3122. If the collected data are not adequate, then the controller restarts the test session as is represented by step 3124, by returning to an earlier step, such as step 3104, 3106 etc.

Some embodiments of the airway device include capabilities to communicate with caregivers, such as physicians, nurses, family, neighbors, etc. This communication may happen wirelessly via a wi-fi connection or via a cell connection. Alternatively, the communication may happen in a wired configuration. This communication may be with a network or directly peer-to-peer. The network may be the internet, intranet or other network. These communications may help caregivers monitor a user's health status. For example, data may be communicated which relates to congestive heart failure, PAC, pulmonary issues (such as COPD, emphysema, asthma, lung capacity, lung sounds, asthma, shortness of breath, etc.), other cardiac issues (such as atrial fibrillation, valve regurgitation or prolapse, plaque buildup, heart murmurs, heart sounds, etc.), diabetes, stroke, nutrition, medication adherence, routine adherence, physical strength, physical dexterity, hydration, temperature, blood pressure, heart rate, respiratory rate, tidal volume, ECG, breathing sounds, saliva chemistry, breath chemistry, steadiness/tremors, hearing, etc. These conditions may be monitored over time and changes in patterns may indicate a problem and may be communicated to one or more caregivers. Alternatively, certain thresholds may be predefined or "learned" from the data which trigger an alert to a caregiver. Effectiveness of various treatments may also be monitored over time.

In situations where data is transmitted via a network, privacy is of utmost concern. The data may be encrypted, anonymized etc. to adhere to HIPAA standards. In addition, the identity of the user may be confirmed based on data consistency (data for a session is similar enough to the data of past sessions), fingerprint ID (may be gathered from the pads on the handheld portion of the device or elsewhere, such as on a mobile phone screen), DNA ID (may be gathered from saliva or elsewhere), survey questions etc.

More specifically, pulmonary diseases, such as COPD, emphysema, asthma etc. may be monitored by a spirometer, or other way of measuring breath flow. For example, breath flow may be measured by ultrasonic, Doppler, mechanically (as in a pinwheel type device) etc. A microphone may be incorporated into the airway device to detect lung sounds such as crackling or wheezing, which may be an indicator of fluid in the lungs or other problems with the lungs. Adherence and/or effectiveness of medications may be monitored by looking at this type of data over time, to see if symptoms/conditions worsen or get better. Also, chemical markers in the breath and saliva can be monitored to confirm use of certain medications/treatments.

In addition to monitoring heart failure conditions (described extensively herein), other cardiovascular conditions such as AFIB (atrial fibrillation), valve issues (regurgitation, irregularities, etc.), plaque buildup may also be monitored. For example, a microphone may be incorporated into the airway device to detect heart sounds such as those associated with valve regurgitation, irregularities, and/or atrial fibrillation. One or more ECG sensors may be incorporated into the handheld portion of the airway device or elsewhere on the device to monitor the ECG. In addition, PAC (described elsewhere herein) is also useful in monitoring heart conditions other than heart failure. For example, PAC may be used to monitor the buildup of plaque, or other issues within the cardiovascular arteries.

Figure 32:
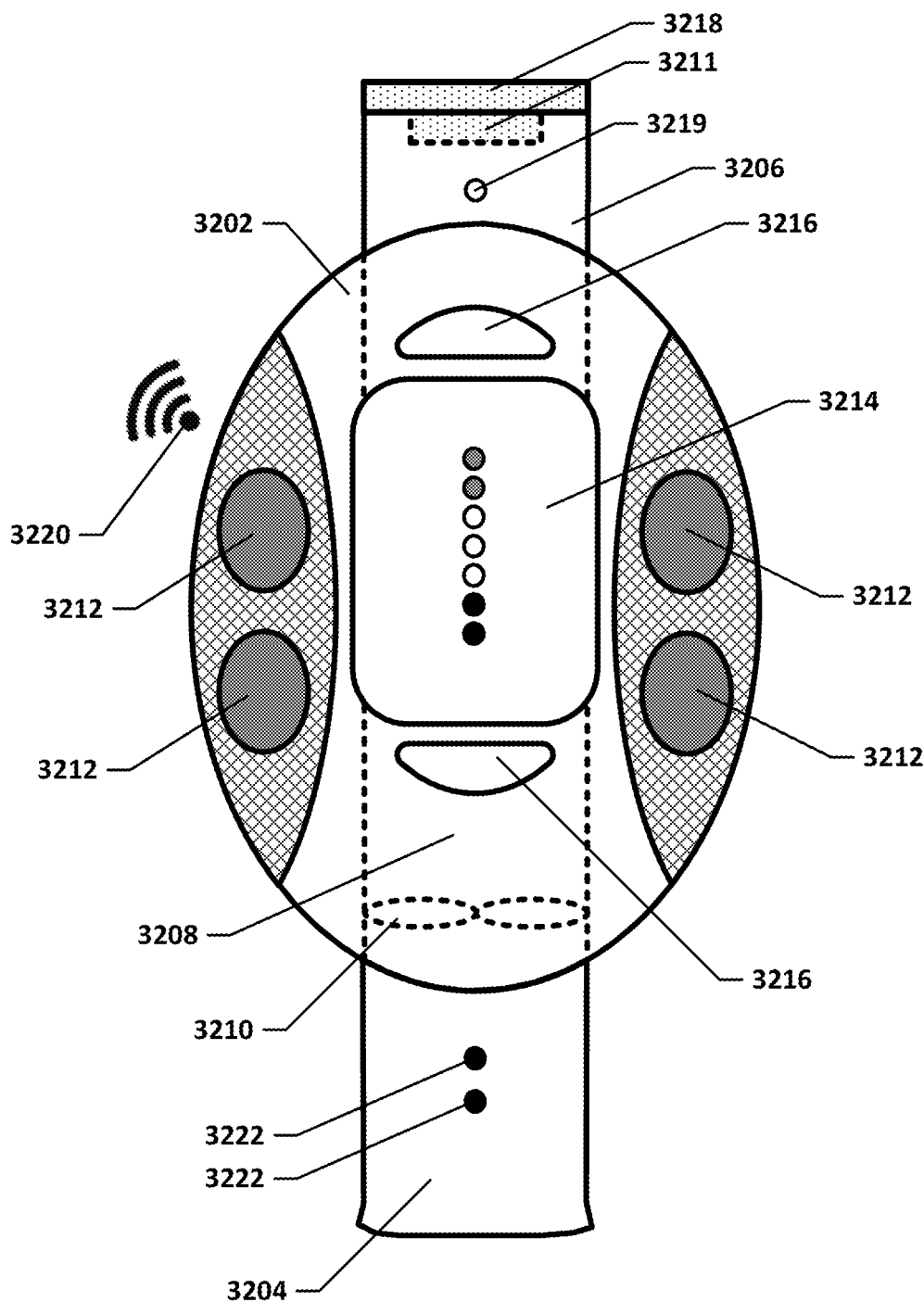
FIG. 32 shows an embodiment of the airway device which incorporates a spirometer, and other features.

FIG. 32 shows an embodiment of the airway device which incorporates a spirometer, or flow meter. Sensor hand-piece 3202 includes mouthpiece 3204, endpiece 3206, inner lumen 3208, which connects the mouthpiece and the endpiece, pinwheel 3210, pressure transducer 3211, electrodes or sensors 3212 (which may be on top and/or bottom of the sensor hand-piece), display 3214, buttons 3216, cap 3218, resistance control orifice 3219, and transmission capability, 3220. This embodiment may also include other sensors 3222, such as a temperature sensor, microphone, analyte sensor, etc. either inside the mouthpiece/inner lumen/endpiece, or on the outside of the mouthpiece, in contact with the mouth. A temperature sensor may be inside the mouthpiece, or on the outside of the mouthpiece. A microphone may be inside the mouthpiece or inner lumen. An analyte sensor may be on the outside of the mouthpiece.

The airway device shown in FIG. 32 can be used to diagnose and/or monitor pulmonary diseases, such as COPD, emphysema, asthma, in addition to monitoring cardiovascular health. The device is used with cap 3218 removed to assess pulmonary function. In this mode, the user is prompted by the controller to breathe through mouthpiece 3204, either regularly, or in a forced exhale, so that air flows through mouthpiece 3204, past sensors 3222 which may assess breath temperature, sounds, etc., past pinwheel 3210, which senses air flow, and through inner lumen 3208 and exits the device via endpiece 3206, which is open in this mode.

The device is used with cap 3218 in place to assess cardiovascular health. In this mode, the user is prompted by the controller to contact sensors 3212 in a particular way (sensor contact may also be requested by the controller in pulmonary function mode). The user is also prompted by the controller to exhale into the mouthpiece with the throat open, for example via a MVM. Indicators on display 3214, or audible or tactile indicators may help the user perform the MVM at the required pressure for the required period of time, and in the required position(s). Buttons 3216 may serve other functions, such as on/off, display settings, navigation etc. Data may be transmitted from the device wirelessly via Bluetooth, wifi, cellular network etc. Data may also be transferred via a wired connection, such as USB. Pressure transducer 3211 may be incorporated into cap 3218 or may be incorporated into the sensor hand-piece body. Display 3214 may be on the sensor hand-piece body, or may be on a mobile device, such as a mobile phone or tablet, or the display may be incorporated into both devices.

As mentioned elsewhere herein, cardiogenic oscillations are detectable during a "modified Valsalva maneuver" or MVM, where the user has his/her throat open (i.e., leaving the glottis and/or epiglottis open) during exhalation against pressure. This is referred to as a "modified Valsalva maneuver" or MVM. The patient/user may be prompted to exhale within a specific pressure range and for a specific time period. The user may be prompted by the controller, or instructed, to perform the MVM within the proper parameters (open throat, pressure, and time).

Figure 34:
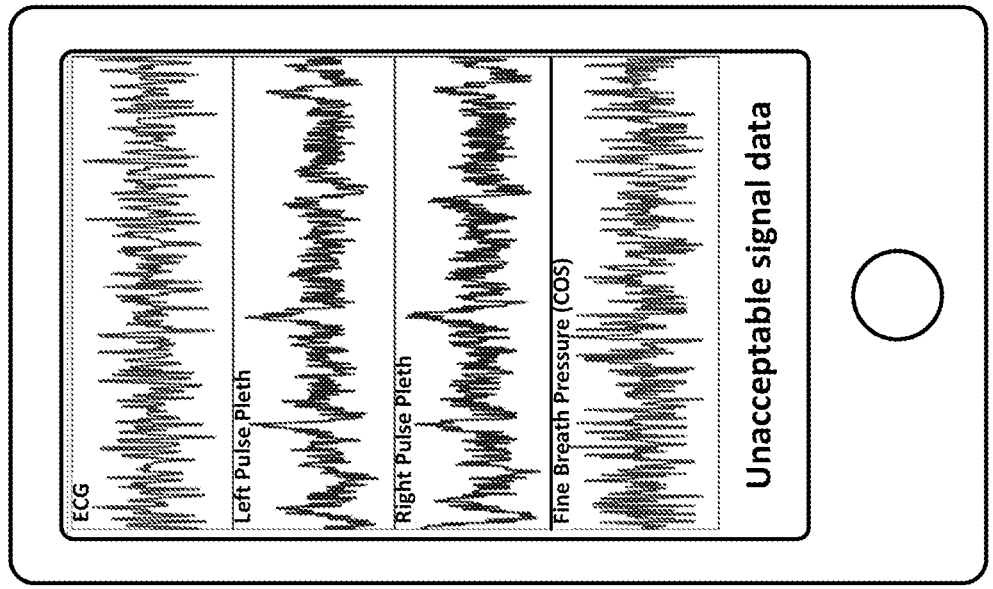
FIGS. 33 and 34 show example screens of a training app.
Figure 33:
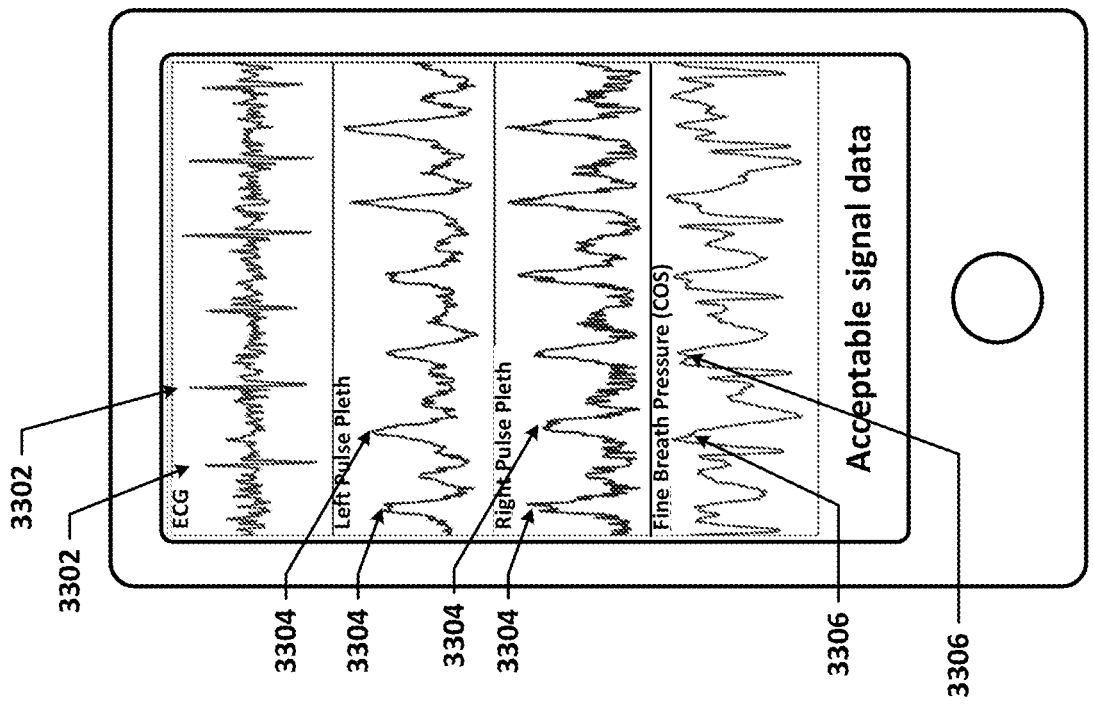

To ensure that the user is performing the MVM properly, the user may be instructed to perform use a training app. The training app may be part of the controller function (i.e., an app on a mobile phone, which is in communication with a sensing hand-piece). The training app may prompt the user to place the mouthpiece in his mouth, and place his fingers/thumbs on the sensors on the sensor hand-piece. The training app may then ask the user to exhale into the mouthpiece while holding the sensor hand-piece. The user will be asked to exhale with his throat open, at a steady pressure indicated on the display, for a set time period. For example, the user may be asked to exhale at a steady pressure, for 5 seconds, so that a light indicator on the display remains within an indicated range. The app may then display the results of the test. Examples of displayed data are shown in FIGS. 33 and 34. FIG. 33 shows examples of acceptable ECG data, left photoplethysmograph data, right photoplethysmograph data, and cardiogenic oscillation (breath fine pressure) data. FIG. 34 shows examples of unacceptable ECG data, left photoplethysmograph data, right photoplethysmograph data, and cardiogenic oscillation (breath fine pressure) data. In some embodiments, the user (or a physician, assistant, technician or nurse) will be prompted to visually assess the data curves to determine whether they are acceptable or unacceptable. For example, an acceptable ECG curve will have noticeable and periodic R-wave spikes 3302 that represent the user's heartbeat. An acceptable photoplethysmograph curve will have noticeable and periodic spikes 3304 that represent the user's heartbeat. An acceptable COS curve will have noticeable and periodic peaks 3306.

In some embodiments, the signal curve data for the various sensors is analyzed for shape in a similar manner by the controller. In these embodiments, the data may not be displayed on the display. The controller (or user) may only need one acceptable gating signal (ECG or either photoplethysmograph signal) and an acceptable COS signal to prompt the user to continue to the actual data collection. For example, if the left photoplethysmograph signal and the COS signal are acceptable, the left photoplethysmograph signal may be used to gate the COS signal.

If the ECG signal is unacceptable, the user may be prompted by the controller to contact the ECG sensor differently, for example with more pressure, less pressure, or with more sensor coverage. If the photoplethysmograph signal is unacceptable, the user may be prompted by the controller to contact the ECG sensor differently, for example with more, less pressure or with more sensor coverage. If the COS signal is unacceptable, the user may be prompted by the controller to breathe differently, for example, to hold breath more steady (if rough pressure sensor has determined that the exhale pressure was not within range for long enough, or if COS signal curve does not have identifiable peaks), to exhale for longer (if rough pressure sensor has determined that the exhale pressure was not within range for long enough or if not enough identifiable peaks are available), to exhale with more or less pressure, to open his throat while exhaling (if COS curve does not have identifiable peaks) etc.

Once the user has obtained acceptable data via the training app, he may move on to actual data collection for analysis and trending. The user may periodically be prompted by the controller to fill out a survey concerning his/her health. The survey may be requested once/data collection session, or at any other interval, for example once/day, once/week, once/month, etc.

FIGS. 35 and 36 show examples of survey screens displayed to the user by the controller. One example of a survey which may be used is the Minnesota Living With Heart Failure Questionnaire.

Some embodiments of the airway device may include one or more accelerometers on the handheld portion of the device. Data from accelerometers may be used to sense the position of the device to ensure proper positioning (for example, is the subject lying down or sitting based on the angle), or the existence or worsening of tremors.

Some embodiments of the airway device may include a speaker to introduce sounds into the mouthpiece/tube. Some embodiments may include a hearing test—for example, touching certain sensors on the handheld portion in response to auditory tones created by the controller.

Some embodiments of the airway device may include impedance sensors (for example on the mouthpiece, or on the handheld portion, contacting one or both hands). For example, 2 separate impedance sensors may be on the handheld portion—one for the left hand and one for the right hand, so that impedance measurements can be taken across hands. Impedance measurements can determine user hydration. Data from the impedance sensors may be used alone or in conjunction with data from other sensors. For example, impedance data may be used in conjunction with PAC data to determine user hydration. Impedance measurements may also be used to determine user body weight and/or fat composition.

Some embodiments of the airway device may be able to monitor diabetes, for example by monitoring analytes in saliva, breath or on the skin.

Some embodiments of the airway device collect data on usage patterns in addition to physiological data to determine whether the user is straying from routine. Straying from routine may be an indicator of a health issue such as stroke, dementia, etc.

Some embodiments of the airway device include one or more strain gauges on the handheld portion to determine finger pressure. These data may be used for device usage compliance (is the user positioning his/her fingers appropriately on the device) and/or for physiological data such as finger strength or steadiness. Some embodiments may include a dexterity test, where the user is asked to touch certain sensors quickly, or in a test pattern, which is indicated by sounds and/or lights or other indicators produced by the controller.

Some embodiments of the airway device are calibrated using data across multiple users of multiple disease states. Alternatively or additionally, some embodiments of the airway device may be calibrated using data learned from the subject user over time, optionally augmented with surveys or other means of obtaining health related information.

What is claimed is:

1. A system having an airway device comprising:
    a mouthpiece section and an opening section defining one or more airway lumens therethrough;
    a first sensor in fluid communication with the one or more airway lumens and configured to detect an airway pressure when a user inhales or exhales through the one or more airway lumens;
    a second sensor positioned upon a hand-piece for contact against a portion of the user and configured to detect a physiological signal from the user, wherein the first sensor and/or second sensor are further configured to detect heartbeats from the user; and a controller in communication with the first and second sensors, wherein the controller is programmed to synchronize pressure oscillations in the airway pressure received from the first sensor with heartbeats received from the first sensor or the second sensor, and wherein the controller is further programmed to gate curves of the pressure oscillations in the airway pressure to a timing of the heartbeats; to generate an overlay of two or more individual gated curves of the pressure oscillations, and to calculate an average or median of the overlaid two or more individual gated curves of the pressure oscillations in the airway pressure in order to allow for analysis of shape of the two or more gated curves;

wherein the controller is further programmed to guide the user through a predetermined breathing procedure with feedback for altering a breathing pattern by the user when detecting the physiological signal until a breathing goal is achieved whereby the user is further prompted by the controller to cease altering the breathing pattern.

2. The device of claim 1 wherein the second sensor comprises an electrocardiogram sensor.

3. The system of claim 1 wherein the first sensor is configured to detect cardiogenic oscillations in the airway pressure.

4. The system of claim 3 wherein the controller is programmed to synchronize the pressure oscillations within the airway pressure with a systolic pulse data or a diastolic pulse data detected from the physiological signal.

5. The device of claim 3 wherein the controller is programmed to correlate the pressure oscillations within the airway pressure with a QRS complex detected from the physiological signal.

6. The system of claim 1 wherein the second sensor comprises a pulse oximeter or photoplethysmograph sensor.

7. The system of claim 1 wherein the second sensor is positioned upon a surface of the hand-piece such that the second sensor is configured to contact a hand or finger of the user.

8. The system of claim 1 wherein the controller is further programmed to sense the airway pressure during exhalation from the user and to determine whether the airway pressure is within a predetermined range.

9. The system of claim 1 wherein the controller is further programmed to detect a resulting exhalation from the user.

10. The system of claim 9 wherein the controller is programmed and configured to indicate via a display to the user whether the resulting exhalation is within a predetermined pressure range.

11. The system of claim 9 wherein the controller is further programmed and configured to provide a feedback via a display to the user relating to parameters of the resulting exhalation.

12. The system of claim 1 further comprising a server located remotely from the device, wherein the device is in communication with the server.

13. The system of claim 1 wherein the controller is further programmed and configured to provide a prompt via a display to the user to change a physical position of the user.

14. The system of claim 13 wherein the physical position comprises a supine or sitting position.

15. The system of claim 1 further comprising a restrictor which restricts airflow through the one or more airway lumens.

16. The system of claim 1 wherein the controller comprises a smartphone in communication with the first and second sensors.

17. The system of claim 1 further comprising a third sensor in fluid communication with the one or more airway lumens and configured to detect rough airway pressure through the one or more airway lumens.

18. The system of claim 1 wherein the curves of the pressure oscillations are gated to the timing of the heartbeats by determining a length of the heartbeats in order to isolate cardiogenic oscillations for identifying changes in the cardiogenic oscillations as an indicator of patient health.

19. The system of claim 1 wherein the second sensor is configured to detect the physiological signal from the user relating to heartbeats, wherein the controller is further programmed to generate curves of the pressure oscillations based on the airway pressure detected via the first sensor and gate the curves of the pressure oscillations in the airway pressure to timing of the heartbeats detected by the second sensor.

20. The system of claim 19 wherein the controller is programmed to prompt the user to exhale at a consistent pressure.

21. The system of claim 20 wherein the controller is programmed to prompt the user to exhale at the consistent pressure for a predetermined period of time.

22. The system of claim 19 wherein the controller is programmed to prompt the user to exhale with an open throat at a consistent pressure.

23. The system of claim 19 wherein the controller is programmed to prompt the user to perform a modified Valsalva maneuver for a predetermined period of time.

24. The system of claim 1 wherein the controller is further programmed to synchronize the pressure oscillations in the airway pressure received from the first sensor with the heartbeats when the user inhales or exhales naturally or normally.

25. The system of claim 1 wherein the controller is further programmed to synchronize the pressure oscillations in the airway pressure received from the first sensor with the heartbeats when the user inhales or exhales when prompted by the controller.

26. A method of correlating physiologic parameters, comprising:
  detecting via a first sensor an airway pressure of a user while inhaling or exhaling through one or more airway lumens of a respiration device having a mouthpiece section and an opening section;
  detecting via a second sensor positioned upon a hand-piece of the respiration device a physiological signal sensed from the user in contact with the second sensor;
  detecting heartbeats via the first sensor or second sensor;
  synchronizing via a controller pressure oscillations in the airway pressure received from the first sensor with a timing of heartbeats received from the second sensor;
  gating curves of the pressure oscillations in the airway pressure to the timing of heartbeats;
  generating an overlay of two or more individual gated curves of the pressure oscillations;
  calculating an average or median of the overlaid two or more individual gated curves of the pressure oscillations in the airway pressure in order to allow for analysis of shape of the two or more gated curves;
  guiding the user through a predetermined breathing procedure with feedback for altering a breathing pattern by the user when detecting the physiological signal until a breathing goal is achieved; and prompting the user by the controller to cease altering the breathing pattern.

27. The method of claim 26 wherein detecting via the first sensor comprises detecting cardiogenic oscillations in the airway pressure.

28. The method of claim 27 wherein synchronizing via the controller comprises synchronizing the pressure oscillations with a timing of a systolic pulse data or a diastolic pulse data detected from the physiological signal.

29. The method of claim 27 wherein correlating via a controller comprises correlating the pressure oscillations with a timing of a QRS complex detected from the physiological signal.

30. The method of claim 26 wherein detecting via a second sensor comprises detecting via a pulse oximeter or photoplethysmograph.

31. The method of claim 26 wherein detecting via a second sensor comprises detecting the physiological signal through a hand or finger of the user in contact with the second sensor.

32. The method of claim 26 wherein detecting via the first sensor comprises detecting the exhaling from the user and determining whether the airway pressure is within a predetermined range.

33. The method of claim 26 further comprising transmitting information from the respiration device to a server located remotely from the respiration device.

34. The method of claim 26 further comprising prompting the user to change a physical position of the user.

35. The method of claim 34 wherein the physical position comprises a supine or sitting position.

36. The method of claim 26 further comprising restricting airflow through the one or more airway lumens of the respiration device prior to synchronizing via the controller.

37. The method of claim 26 further comprising transmitting information between the respiration device and a smartphone in communication with the first and second sensors.

38. The method of claim 26 further comprising detecting via a third sensor in fluid communication with the one or more airway lumens rough airway pressure through the one or more airway lumens.

39. The method of claim 26 wherein gating curves of the pressure oscillations comprises determining a length of the heartbeats in order to isolate cardiogenic oscillations for identifying changes in the cardiogenic oscillations as an indicator of patient health.

40. The method of claim 26 wherein the physiological signal sensed from the user relates to the heartbeats.

41. The method of claim 40 wherein guiding the user further comprises prompting the user to exhale at a consistent pressure.

42. The method of claim 41 further comprising prompting the user to exhale at the consistent pressure for a predetermined period of time.

43. The method of claim 40 wherein guiding the user further comprises prompting the user to exhale with an open throat at a consistent pressure.

44. The method of claim 40 wherein guiding the user further comprises prompting the user to perform a modified Valsalva maneuver for a predetermined period of time.

45. The method of claim 26 wherein detecting via the first sensor comprises detecting the airway pressure of the user while inhaling or exhaling naturally or normally.

46. The method of claim 26 wherein detecting via the first sensor comprises detecting the airway pressure of the user while inhaling or exhaling with prompting by the controller.

* * * * *